US010603542B1

(12) United States Patent
Smyser et al.

(10) Patent No.: US 10,603,542 B1
(45) Date of Patent: Mar. 31, 2020

(54) SYSTEMS, METHODS, AND APPARATUS FOR ISOMETRIC, ISOKINETIC, ISOTONIC, AND ISODYNAMIC EXERCISE

(71) Applicant: MD Systems, Inc., Westerville, OH (US)

(72) Inventors: Michael A. Smyser, New Smyrna Beach, FL (US); David Ferguson, New Albany, OH (US); Thomas VanFossen, Lewis Center, OH (US)

(73) Assignee: MD Systems, Inc., Westerville, OH (US)

( * ) Notice: Subject to any disclaimer, the term of this patent is extended or adjusted under 35 U.S.C. 154(b) by 36 days.

(21) Appl. No.: 15/788,735

(22) Filed: Oct. 19, 2017

Related U.S. Application Data

(60) Provisional application No. 62/410,271, filed on Oct. 19, 2016.

(51) Int. Cl.
*A63B 23/16* (2006.01)
*A63B 24/00* (2006.01)
(Continued)

(52) U.S. Cl.
CPC ............ *A63B 23/16* (2013.01); *A61B 5/1125* (2013.01); *A63B 21/002* (2013.01);
(Continued)

(58) Field of Classification Search
CPC . A61B 5/1125; A63B 21/002; A63B 21/0023; A63B 21/0083; A63B 21/0087;
(Continued)

(56) References Cited

U.S. PATENT DOCUMENTS 3,672,219 A * 6/1972 Van Patten ............... A61B 5/22
73/379.02
4,553,746 A * 11/1985 Lee ......................... A63B 23/16
482/49
(Continued)

FOREIGN PATENT DOCUMENTS

WO        8702567 A1    5/1987
WO    2004032701 A2    4/2004

OTHER PUBLICATIONS

Choquette, et al., "Blood Pressure Reduction in 'Borderline' Hypertensivies Following Physical Training" Can. Med. Assoc. J. 1108:699-703, 1973.

(Continued)

*Primary Examiner* — Joshua Lee
(74) *Attorney, Agent, or Firm* — Wood Herron & Evans LLP

(57) ABSTRACT

Adapter devices that adapt hand exercise devices to permit the use thereof by persons of widely variable hand size, and permit the use thereof in exercises or tests other than the isometric exercises and tests for which they are known. The adapters provide replacement grips and couple force applied to those replacement grips to the handgrip surfaces of the hand exercise device. One version of the adapter includes a piston and cylinder connected to the replacement grips that move in a range of motion during a hand exercise or test, to allow for isotonic, isokinetic or isodynamic hand exercises. Other versions of the adapter use removable cams, screw cams, rotary cams, and sliding cams to adjust the distance between the grips for the size of the user's hand. A further adapter provides replacement grip surfaces sized for a user's finger and thumb for performing a pinch exercise or test.

12 Claims, 25 Drawing Sheets

(51) Int. Cl.
| | |
|---|---|
| *A63B 21/002* | (2006.01) |
| *A63B 21/008* | (2006.01) |
| *A63B 21/00* | (2006.01) |
| *A63B 71/06* | (2006.01) |
| *A61B 5/11* | (2006.01) |

(52) U.S. Cl.
CPC ...... *A63B 21/0023* (2013.01); *A63B 21/0083* (2013.01); *A63B 21/0087* (2013.01); *A63B 21/4035* (2015.10); *A63B 24/0062* (2013.01); *A63B 24/0087* (2013.01); *A63B 71/0622* (2013.01); *A63B 2024/0093* (2013.01); *A63B 2220/20* (2013.01); *A63B 2220/51* (2013.01); *A63B 2225/09* (2013.01)

(58) Field of Classification Search
CPC . A63B 21/4035; A63B 23/16; A63B 24/0062; A63B 24/0087; A63B 71/0622; A63B 2024/0093; A63B 2220/20; A63B 2024/51; A63B 2225/09
See application file for complete search history.

(56) References Cited

U.S. PATENT DOCUMENTS

| | | | |
|---|---|---|---|
| 4,884,445 A | 12/1989 | Sadoff et al. | |
| 4,939,933 A * | 7/1990 | Curran | A61B 5/103 482/8 |
| 4,949,729 A | 8/1990 | Haski | |
| 5,398,696 A | 3/1995 | Wiley | |
| 5,904,639 A | 5/1999 | Smyser et al. | |
| 6,026,684 A | 2/2000 | Calder | |
| 6,217,504 B1 | 4/2001 | Phillips | |
| 6,358,187 B1 | 3/2002 | Smith | |
| 6,962,569 B2 | 11/2005 | Smyser et al. | |
| 7,448,265 B2 | 11/2008 | Smyser et al. | |
| 9,782,624 B2 * | 10/2017 | Braier | A63B 23/16 |
| 9,857,261 B2 * | 1/2018 | Hogrel | A61B 5/225 |
| 2005/0101461 A1 | 5/2005 | Johnson | |
| 2008/0132388 A1 | 6/2008 | Clem et al. | |
| 2012/0255355 A1* | 10/2012 | Xu | A61B 5/225 73/379.02 |
| 2016/0220863 A1* | 8/2016 | Braier | A63B 23/16 |

OTHER PUBLICATIONS

Chrysant et al., Hemodynamic Effects of Isometric Exercise in Normotensive Hypertensive Subjects: Hypertension, Angiology 1978; 29(5):379-85.
Clarke et al., The duration of sustained contractions of the human forearm at different muscle temperatures, J. Physiol., 1958; 143:454-473.
Gliders, et al., "Endurance Training and Blood Pressure in Normotensive and Hypertensive Adults", Med. Sci. Sports Exerc. 21:629-636, 1989.
Hanson P., et al., "Isometric Exercise: Cardiovascular Responses in Normal and Cardiac Populations", Cardiology Clinics 1987;5(2):157-70.
Harris, et al., "Physiological Response to Circuit Weight Training in Borderline Hypertensive Subjects", Med. Sci. Sports Exerc., 19:246-252, 1987.
Howden et al., The effects of isometric exercise training on resting blood pressure and orthostatic tolerance in humans, Exp. Physiol. 2002; 87.4, pp. 507-515.
Hurley, et al., "Resistive Training Can Induce Coronary Risk Factors Without Altering VO.sub.2 max or Percent Body Fat", Med. Sci. Sports Exerc. 20:150-154, 1988.
Kiveloff et al., Brief Maximal Isometric Exercise in Hypertension, J. Am Geriatr. Sod. 9:1006-12.
Lind, Editorial: Cardiovascular Responses to Static Exercise (Isometrics, Anyone?), Circulation 1970; 41(2):173-76.
Mathiowetz, et al., "Effect of Elbow Position on Grip and Key Pinch Strength", The Journal of Hand Surgery 10A:694-7, 1985.
Mathiowetz, et al., "Grip and Pinch Strength: Normative Data for Adults", Arch Phys Med Rehabilitation 66:69-72, 1985.
Mathiowetz, et al., "Grip and Pinch Strength: Norms for 6 to 19 Year Olds", The American Journal of Occupational Therapy 40:705-11, 1986.
Mathiowetz, et al., "Reliability and Validity of Grip and Pinch Strength Evaluations", The Journal of Hand Surgery 9A:22-6, 1984.
McGowan et al., Isometric Handgrip Training Improves Endothelial Function in Persons Medicated for Hypertension, Experimental & Clinical Cardiology. 2004; 9(1): 68.
Meredith et al., Exercise Training Lowers Resting Renal But Not Cardiac Sympathetic Activity in Human, Hypertension 1991; 18:575-82.
Mitchell, et al., Static (Isometric) Exercise and the Heart: Physiological and Clinical Considerations, Ann Rev Med 1974;25:369-81.
Preston, A Bissell Healthcare Company, JAMAR.RTM. Hydraulic Hand Dynamometer, Owner's Manual, Copyright 1992.
Sammons Preston, Evaluation: JAMAR.RTM. Hydraulic Hand Dynamometer, Product Advertisement, no date.
Seals, et al., "The Effect of Exercise Training on Human Hypertension: A Review", Med. Sci. Sports Exerc., 16:207-215, 1984.
Vecht, R. J. Grahm GWS, Sever PS. "Plasma Noradrenaline Concentrations During Isometric Exercise." Brit Heart J. 1978;40:1216-20.
Visocchi et al., The effect of isometric arm and leg exercise on resting blood pressure and arterial distensibility in person medicated for hypertension, APS Intersociety meeting: Integrative Biology of Exercise—Abstracts, American College ofCardiology Conference, Austin 2004.
Wiley, et al., "Isometric Exercise Training Lowers Resting Blood Pressure", Med. Sci. Sports Exerc. 29:749-754, 1992.

* cited by examiner

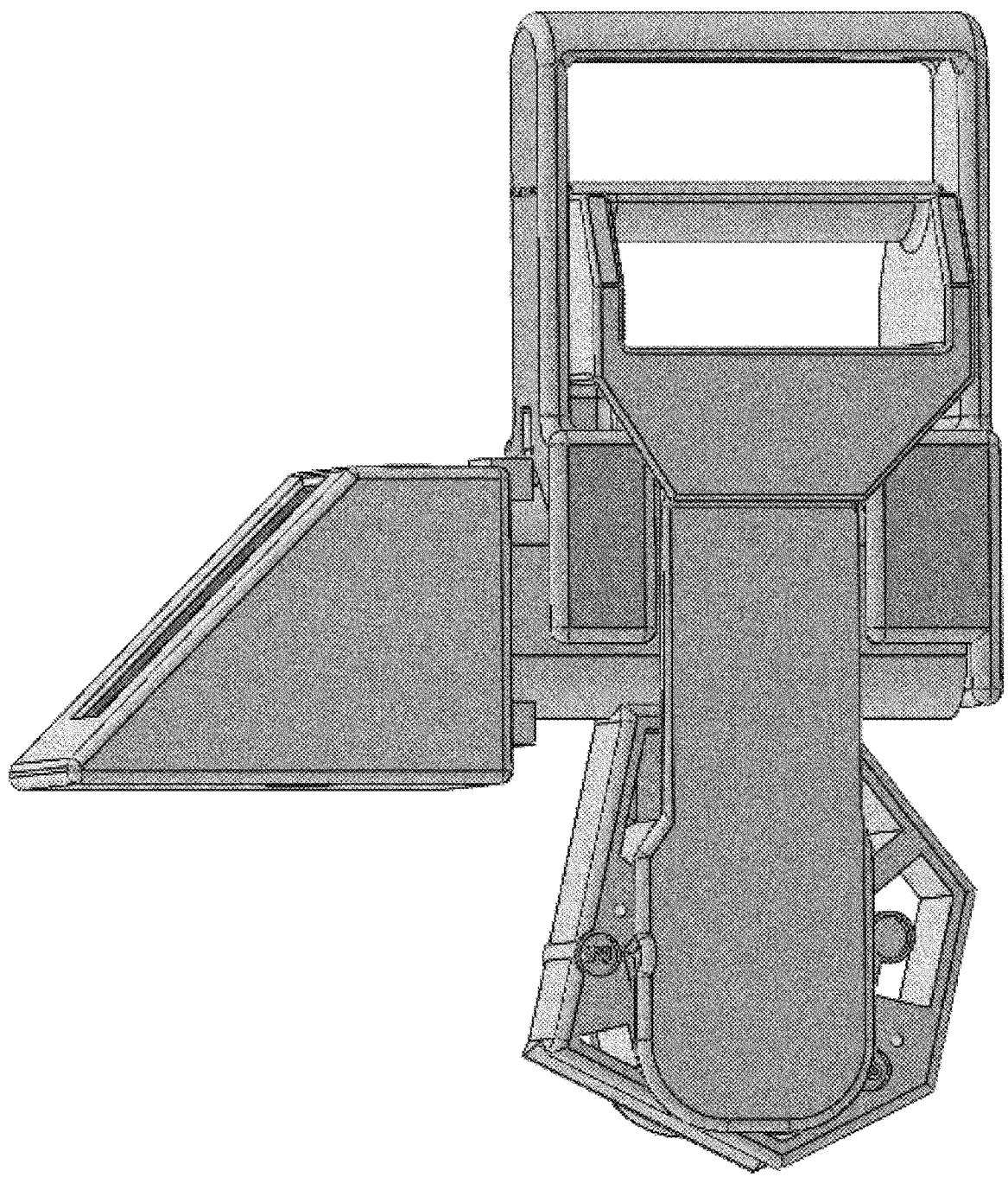

SYSTEMS, METHODS, AND APPARATUS FOR ISOMETRIC, ISOKINETIC, ISOTONIC, AND ISODYNAMIC EXERCISE

RELATED APPLICATIONS

This application is a U.S. non-provisional application claiming priority to provisional application U.S. Ser. No. 62/410,271 filed Oct. 19, 2016, which is incorporated herein in its entirety.

FIELD OF THE INVENTION

This disclosure generally relates to adapters for hand exercise or muscle strength testing devices to accommodate variation in physical dimensions of a user or to permit additional forms of hand exercises or tests of the user.

BACKGROUND OF THE INVENTION

FIG. 1 illustrates a known portable, lightweight device for carrying out isometric exercise and muscular tests, which is described in greater detail in U.S. Pat. Nos. 6,962,569 and 7,448,265 (the disclosure of each of which being hereby incorporated by reference). This apparatus is a handgrip-based dynamometer. Being microprocessor driven, the instrument may be programmed to carry out established diagnostic as well as newly developed grip-based isometric regimens.

When the device of FIG. 1 is employed for carrying out a grip exercise or diagnostic strength test, the diagnostician selects configuration parameters and the instrument provides both visual and audible prompts and cues throughout the procedure. Maximum effort forces of a muscle group for each of the sequence of trials of this procedure may be selected typically by the diagnostician and when so selected are recorded in the instrument memory along with calendar data, and processor-computed values for average grip force, standard deviation of the force values throughout a sequence of tests, and corresponding coefficients of variation. At the termination of the diagnostic procedure, memory recorded test data may be displayable to the diagnostician and may be downloaded through a communications port to a computer facility.

As illustrated in FIG. 1, the instrument or apparatus 110 may have a housing 112 that may be made of an impact resistant material (e.g., acrylonitrile butadiene styrene). FIG. 1 shows that the housing 112 includes a hand grasping portion 114 and an integrally formed interacting portion 116 for visual guidance. Interacting portion 116 supports a readout assembly 118 which is configured as an elongate liquid crystal display (LCD). Two finger-actuable switches 122 and 124 are also located at the interacting portion. Of these switches, switch 122 is designated as a "menu" switch, while switch 124 is designated as a "select" switch. The readout assembly 118 is angularly oriented with respect to the grip axis 126 of the apparatus 110. With this configuration, the user may observe prompts and cues appearing at the readout 118 as represented by the symbolic user eye location 128 and line of sight represented symbolically at arrow 130.

In this example, the hand 132 of the user is grasping the hand grasping portion 114. For the arrangement shown, the hand grasping portion 114 is represented as exhibiting its largest widthwise extent, (e.g., 2⅞ inches). To gain this larger widthwise extent, auxiliary grip components 134 and 136 are employed in conjunction with the hand grasping portion 114. Details relating to these auxiliary grip components can be seen in the above-referenced patents, to be removable as well as universally positionable so as to provide the noted widthwise adjustments in finite increments (e.g., ½ inch increments).

When the instrument of FIG. 1 is used, a protocol is nominated by prescribing nominal parameters of the effort. Each isometric regimen is controlled initially by requiring that a maximum voluntary contraction (MVC) be established for each individual patient or user. Then, the device, user or practitioner may elect parameters of muscular force and timing based on the MVC.

Despite the successes of the device of FIG. 1, the use of this device has been limited for at least two reasons. First, it may only be used for isometric exercises, and further, the device can be difficult to adapt to different body sizes or for uses with other muscle groups such as those in the fingers and thumbs.

SUMMARY OF THE INVENTION

The present invention is directed to overcoming the limitations of this known device by providing adapter devices that adapt hand exercise devices such as that shown in FIG. 1 to permit the use thereof by persons of widely variable hand size, and to permit the use thereof in exercises other than the isometric exercises for the hands or hand grip tests for which they are known.

In one aspect, the adapters described herein are designed to transfer a force applied by a hand on the adapter to the first and second handgrip surface of a handgrip device like the one shown in FIG. 1. The adapter uses a frame which engages the first handgrip surface of the device and a slider that engages the second handgrip surface, so that the user may apply force between a first replacement grip surface on the frame and a second replacement grip surface on the slider, and that force will couple to the handgrip surfaces of the hand exercise device.

In one of the particular embodiments disclosed, the adapter includes a piston and cylinder positioned between the slider and the second handgrip surface of the hand exercise device and movable relative to each other in a range of motion, such that the first and second replacement grip surfaces move relative to each other in a range of motion during a hand exercise. In this embodiment, a displacement sensor is used to measure the distance of motion of the piston and cylinder relative to each other, and an actuator applies force between the piston and cylinder. The displacement sensor and actuator are coupled to a control circuit, which may be a modified version of the circuit already within the hand exercise device, or an external circuit, so that the control circuit can control of the actuator according to a specified force and/or velocity profile to provide a hand exercise to the user according to an isometric, isotonic, isokinetic or isodynamic protocol.

In additional specific embodiments described herein, there is a cam in the adapter that is positionable between the slider and the second handgrip surface of the hand exercise device and can be put in at least a first and a second position, the first and second replacement grip surfaces on the adapter being spaced differently when the cam is in the first position than when the cam is in the second position, to allow for different user physiologies.

In one embodiment using a cam, the cam can be placed between the slider and second handgrip surface, or removed therefore, to adjust the spacing of the grips. In a second embodiment, the cam is a screw member positioned between the slider and the second handgrip surface, which is movable by rotation such that a greater or lesser extent of the cam is positioned between the slider and second handgrip surface. In a third embodiment the cam is a rotary member positioned between the slider and the second handgrip surface, movable by rotation such that a greater or lesser radial extent of the cam is positioned between the slider and second handgrip surface. In a fourth embodiment, the cam is a slidable member position between the slider and the second handgrip surface, movable by sliding such that a thicker or thinker portion of the cam is positioned between the slider and second handgrip surface.

In a still further embodiment, the adapter's replacement grip surfaces are sized for gripping by fewer than all of the fingers of a user's hand, such as by a user's finger and thumb, for performing a pinch exercise or pinch test.

Specifically, one version of an adapter according to the present invention enables not only isometric, but also isokinetic, isotonic, and/or isodynamic hand exercises to be performed according to a user-specific protocol that includes specified exertions to be performed by a user, a specified force and velocity profile governing the exertion, and a specified sequence of repetitions of the exertion, and rest periods. The exercise protocols are tailored to each specific user's needs by measuring the muscle group strength to be exercised and therefore provide enhanced health benefits over the existing handgrip device.

Further embodiments, features, and advantages, as well as the structure and operation of the various embodiments, are described in detail below with reference to the accompanying drawings.

BRIEF DESCRIPTION OF THE DRAWINGS

Embodiments are described with reference to the accompanying drawings. In the drawings, like reference numbers may indicate identical or functionally similar elements.

FIG. 6E is a side perspective view of the adapter of FIG. 6A with the device of FIG. 1 installed therein, showing the rotary member rotated to provide the largest size adjustable gap between the slider and frame of the adapter of FIG. 6E.

Figure 1:
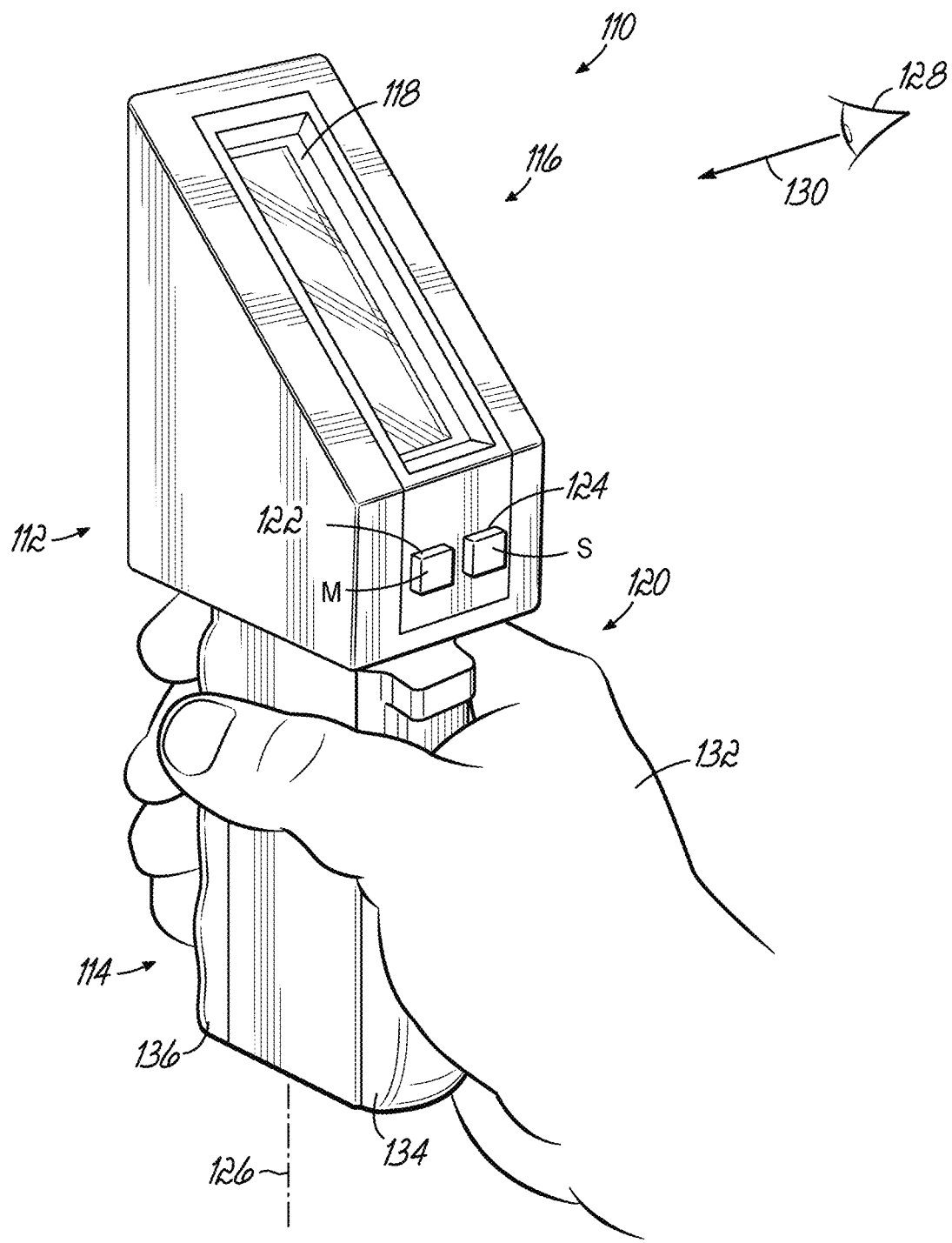
FIG. 1 is a schematic illustration of a handgrip exercise device that is a lightweight, portable, and hand held for carrying out isometric exercise.

The disclosed invention is described below with reference to the accompanying drawings. In the drawings, like reference numbers generally indicate identical, functionally similar, and/or structurally similar elements. The drawing in which an element first appears is indicated by the leftmost digit(s) in the reference number.

DETAILED DESCRIPTION

While the known device of FIG. 1 provides sensors for measuring MVC for a particular individual user, and is adaptable in fixed increments to a user's hand, the adaptability is limited by the size and number of auxiliary grip components, which may not allow adaptation to the particular attributes of an individual user's hand. Furthermore, while the device of FIG. 1 allows for resizing to a user's hand, it does not provide a range of motion or controlled force over a range of motion, and thus cannot establish a protocol of movement over a range of motion; rather, with the device of FIG. 1, effort may only be applied at one static location in the range of motion of a user's hand.

The inventors herein have found that the accurate adaptation of a device to a user's range of motion is critical to effective exercise regimens. Further, the inventors herein have found that effective exercise regimens require a controlled profile of force throughout a user's range of motion, rather than only at one location I that range. These findings have necessitated the advancement and extension of the device of FIG. 1.

The first adapter embodiment described in detail herein provides an adapter for the existing device of FIG. 1 and other similar hand grip exercise devices, that allows variable movement of the hand gripping the device, according to a specified force and/or velocity profile. As such, the first adapter embodiment allows a user to properly perform one or more of isometric (specified force/zero velocity), isokinetic (fixed velocity/constant or variable force), isotonic (constant force/non-zero velocity), and isodynamic (isokinetic or isotonic with isometric) exercises according to a protocol specifically designed for the user, such as based on a measured maximum voluntary contraction (MVC) associated with the user.

The additional adapter embodiments described in detail herein provide adapters for the existing device of FIG. 1 and other similar hand grip exercise devices. Each user (particularly child users) has a unique set of physical dimensions, such as hand size, arm size, torso size, leg size, foot size, height, weight, etc., which result in a unique range of motion of the individual for any particular muscle group being exercised. Adaptation to the range of motion of the user for a particular exercise is an important component of mechanical exercise devices in accordance with the present invention. In particular, the exercise protocols of the type described above should be done in an anatomically correct location in the range of motion for the individual user performing the exercise. More particularly, maximum voluntary contraction (MVC) should be identified at an anatomically correct location in the range of motion of the individual user, and/or the controlled force/velocity profile of an exercise should be provided within the proper range of motion of the individual user. It will be noted that MVC varies across the range of motion and should be measured at an appropriate location in the range of motion for the individual user. Mechanical exercise devices in accordance with the present invention permit MVC measurement to be done at a location in the range of motion which is anatomically correct for the individual user.

The additional adapter embodiments described in detail herein further allow the existing device of FIG. 1 to be used in single finger exercise or multiple finger exercises (finger pinch exercise) and strength tests instead of a full hand exercise. This allows use of the device of FIG. 1 by persons who are seeking to rehabilitate a finger injury, or who have a missing finger or other condition that prevents the device of FIG. 1 from being used appropriately.

The following detailed description refers to the accompanying drawings that illustrate exemplary embodiments. Other embodiments are possible, and modifications may be made to the embodiments within the spirit and scope of this description. Those of ordinary skill in the relevant art with access to the teachings provided herein will recognize additional modifications, applications, and embodiments within the scope thereof and additional fields in which embodiments would be of significant utility. Therefore, the detailed description is not meant to limit the embodiments described below.

References in this specification to "one embodiment," "an embodiment," an "example embodiment," etc., indicate that the embodiment described may include a particular feature, structure, or characteristic, but not every embodiment may necessarily include the particular feature, structure, or characteristic. Moreover, such phrases are not necessarily referring to the same embodiment. Further, when a particular feature, structure, or characteristic may be described in connection with an embodiment, it may be submitted that it may be within the knowledge of one of ordinary skill in the relevant art to affect such feature, structure, or characteristic in connection with other embodiments whether or not explicitly described.

Figure 2:
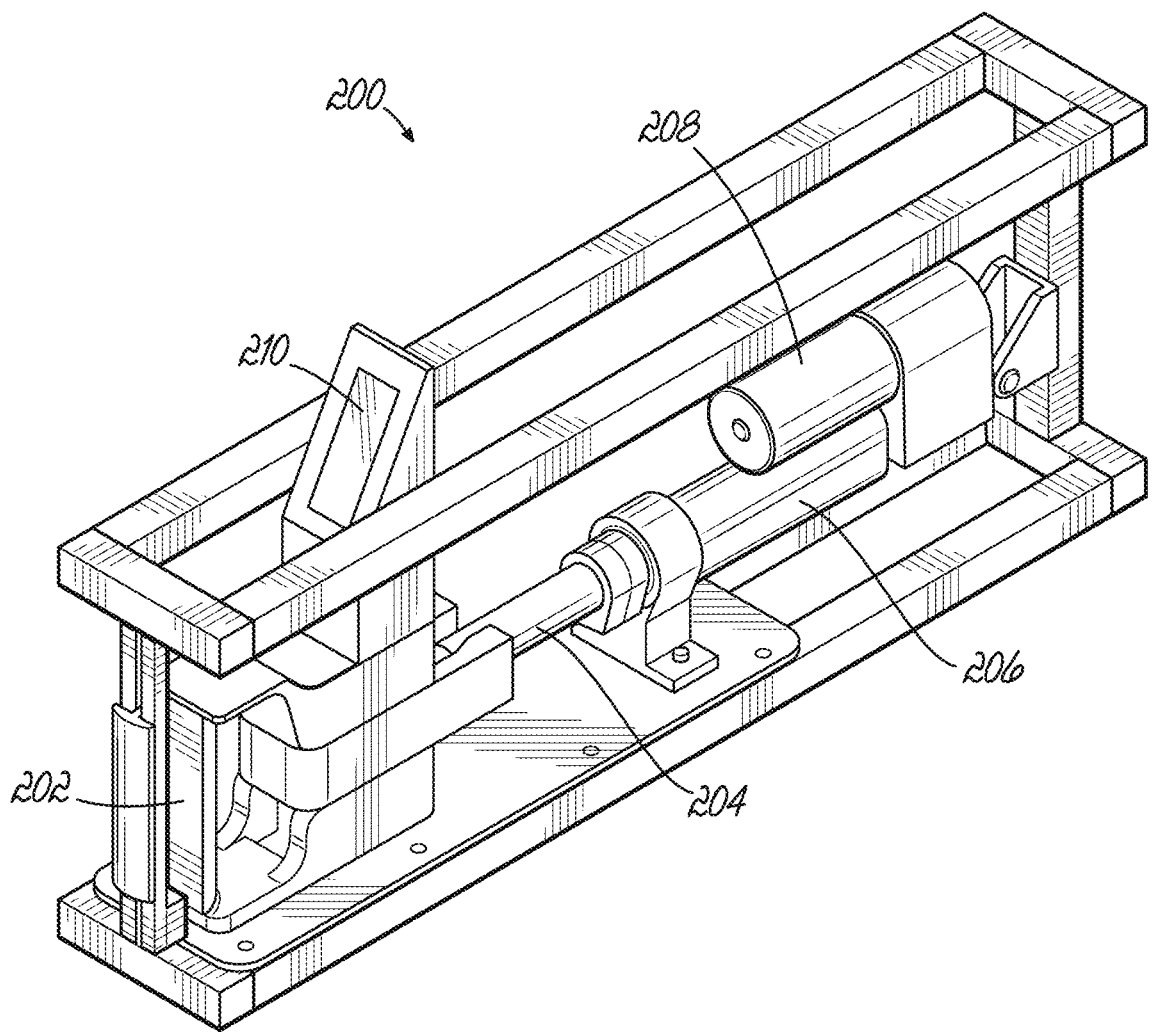
FIG. 2 is a schematic illustration of a further an adapter usable with the handgrip exercise device of FIG. 1, which provides controlled resistance to a user's hand over a range of motion for isotonic or isodynamic exercises.

FIG. 2 is a schematic illustration of a further exercise device 200, according to an embodiment. Device 200 may be assembled as a stand-alone device or may be configured, as shown as an adapter for a conventional handgrip exercise device 210. Device 200 includes a frame to which the other components are mounted, and a slider which is movable within the frame, having a grip portion 202 on its end. The end of the frame and the grip portion may be grasped by the hand of a user while performing an exercise. Specifically, the user's hand may impose a mechanical exertion on the grip portion 202 that imparts a force to other components of the mechanical apparatus. In this example, the grip portion 202 is connected to a piston 204 that is mechanically coupled to a cylinder 206, and is further coupled to the handgrip of the conventional handgrip exercise device 210. The cylinder 206 may be an electrical actuator, mechanical system, or hydraulic or pneumatic cylinder that provides a resistive force in opposition to a force imposed by a user. It will be noted that the force applied by the user's hand is applied to the piston 204 via the handgrip built into the conventional handgrip exercise device 210, and as a result the sensor in the device 210 measures the force provided by the user's hand to the piston 204. The cylinder 206 resists motion of the piston 204 and thus controls the force applied by the user's hand over motion of the piston 204. The cylinder 206 may provide a passive resistive force, or may include an actuator that may impose an additional force that tends to control motion of the piston 204 to specified/controlled velocities and forces, or stated alternatively, require specified/controlled forces to permit motion at specified/controlled velocities. Notably, through the introduction of piston 204 the device of FIG. 2 permits the control of force and/or velocity over a range of motion of the user's hand, not just one location in that range of motion.

To provide the functionality described, the exercise device 200 may further include one or more sensors that measure mechanical displacement of piston 204 in cylinder 206. According to an embodiment, the exercise device 200 may further include a control system that receives signals from a force sensor (e.g., in the FIG. 1 device 210) and displacement sensor (e.g., in the piston/cylinder 204/206) and sends signals to one or more actuators 208 to control the displacement and resistive force imposed by the cylinder 206 on the piston 204 in response to a force imposed by a user on the grip portion 202. In this example, exercise machine 200 may interact with the handgrip device 210 to present feedback on the display thereof, or may have a separate display for providing feedback to the user. This may be done external to the processor in the device 210 of FIG. 1, or may be done by the processor of the device 210 of FIG. 1, by way of a software upgrade and a connection to supply the signal from the displacement sensor to the processor of the device 210 of FIG. 1. As in the example of FIG. 1, a user may observe prompts and cues appearing at an external display device or on the display of the modified version of the device 210.

The embodiments described above with reference to FIGS. 1 and 2 provide a few illustrative examples in which principles of the disclosed invention may be employed. These examples, however, are not limiting and many more examples would be readily apparent to persons of ordinary skill in the art. Such further examples are therefore within the scope of the disclosed invention as defined by the claims presented below.

Figure 3:
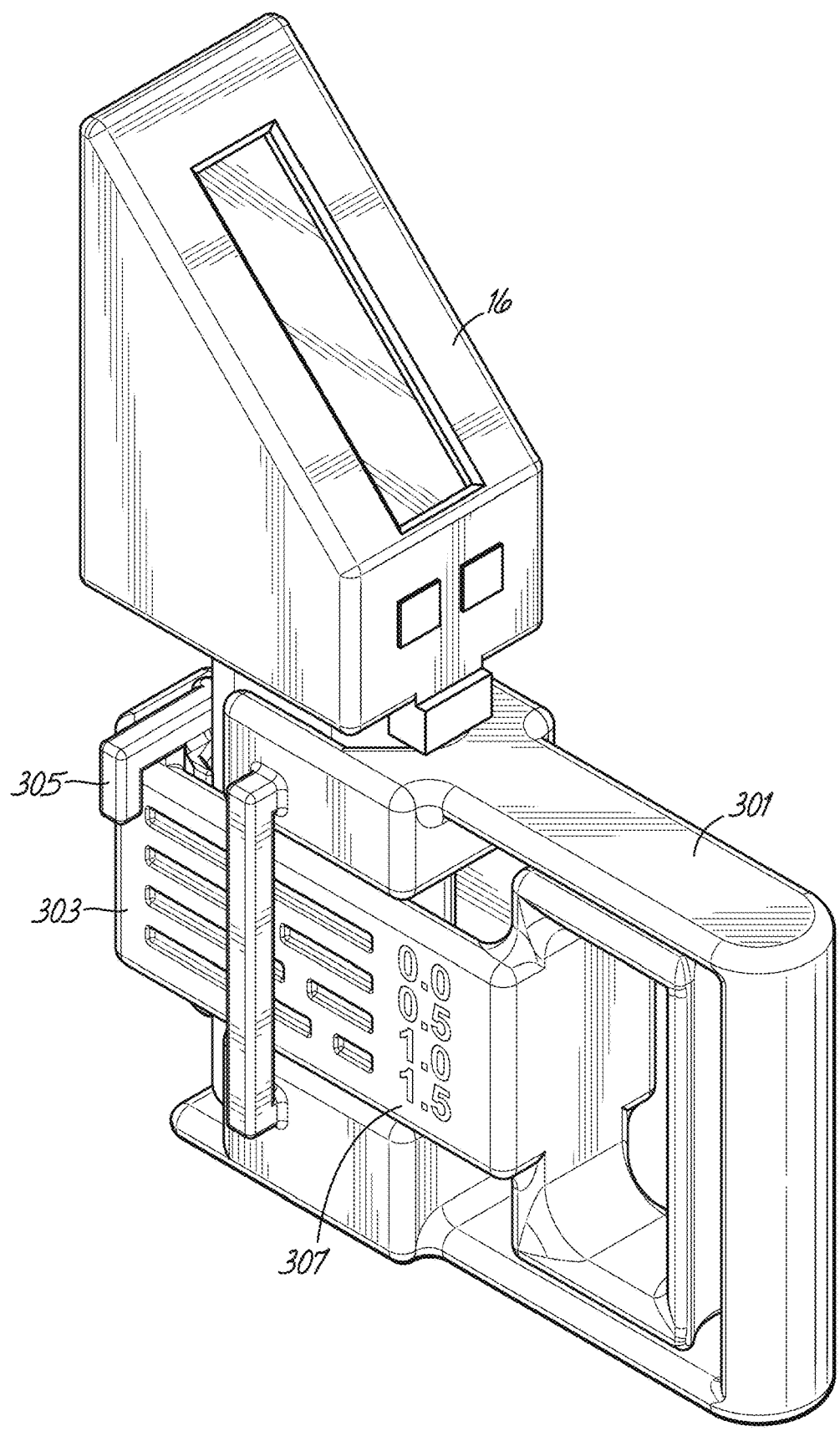
FIG. 3 is a perspective drawing of an adapter usable with the hand exercise device of FIG. 1 to adapt the device for use with hands of various sizes, by the provision of a substitute handle having an adjustable thickness controlled by the insertion of adaptive inserts.
Figure 4A:
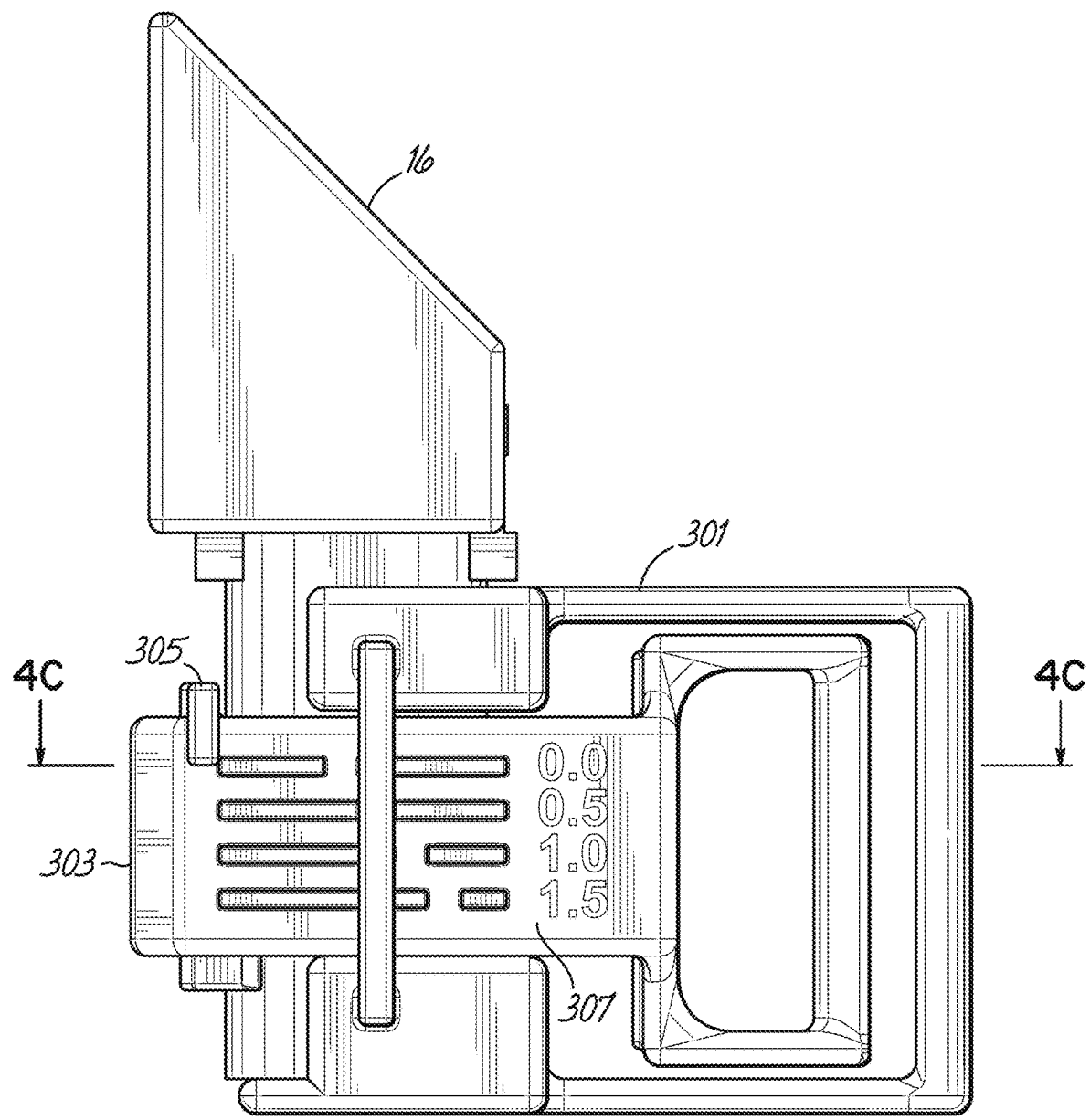
FIG. 4A is a side view of the adapter of FIG. 3.

Specifically, the device of FIG. 1 disclosed above may be expanded for use by smaller persons or children by the use of a handgrip adapter. FIGS. 3 and 4A are perspective and side views of an adapter usable with a hand exercise device 16 of the type shown in FIG. 1. The adapter of FIGS. 3 and 4A adapts the hand exercise device 16 for use with smaller hands, by providing a substitute grip extending from and coupled to the built-in grip of the device 16. The substitute grip includes a frame 301 mounted upon the hand exercise device 16, and a slider 303 which slides within the frame and surrounds the distal surface (surface facing away from the user) of the hand exercise device 16 so that squeezing effort between the slider and frame applies pressure to the grip incorporated into the hand exercise device 16.

The thickness of the substitute grip provided by the slider 303 and frame 301 is adjustable, for example using inserts placed between the slider and the distal surface of the hand exercise device 16. In FIGS. 3 and 4A the smallest such insert 305 is in place. Other alternatives include the use of rotating cams, or adjustments using screws (see FIG. 4D) or the like.

As seen in FIGS. 3 and 4A, the sliding handgrip and/or frame may include a sizing scale 307 indicating the adapted size of the substitute grip between the slider and frame. With the smallest insert 305 in place the adapted size of the substitute grip is 0.5, but with other inserts it may range to 1.0 or 1.5 to accommodate various smaller hand sizes. No insert is associated with size 0.0 on the scale.

Figure 4B:
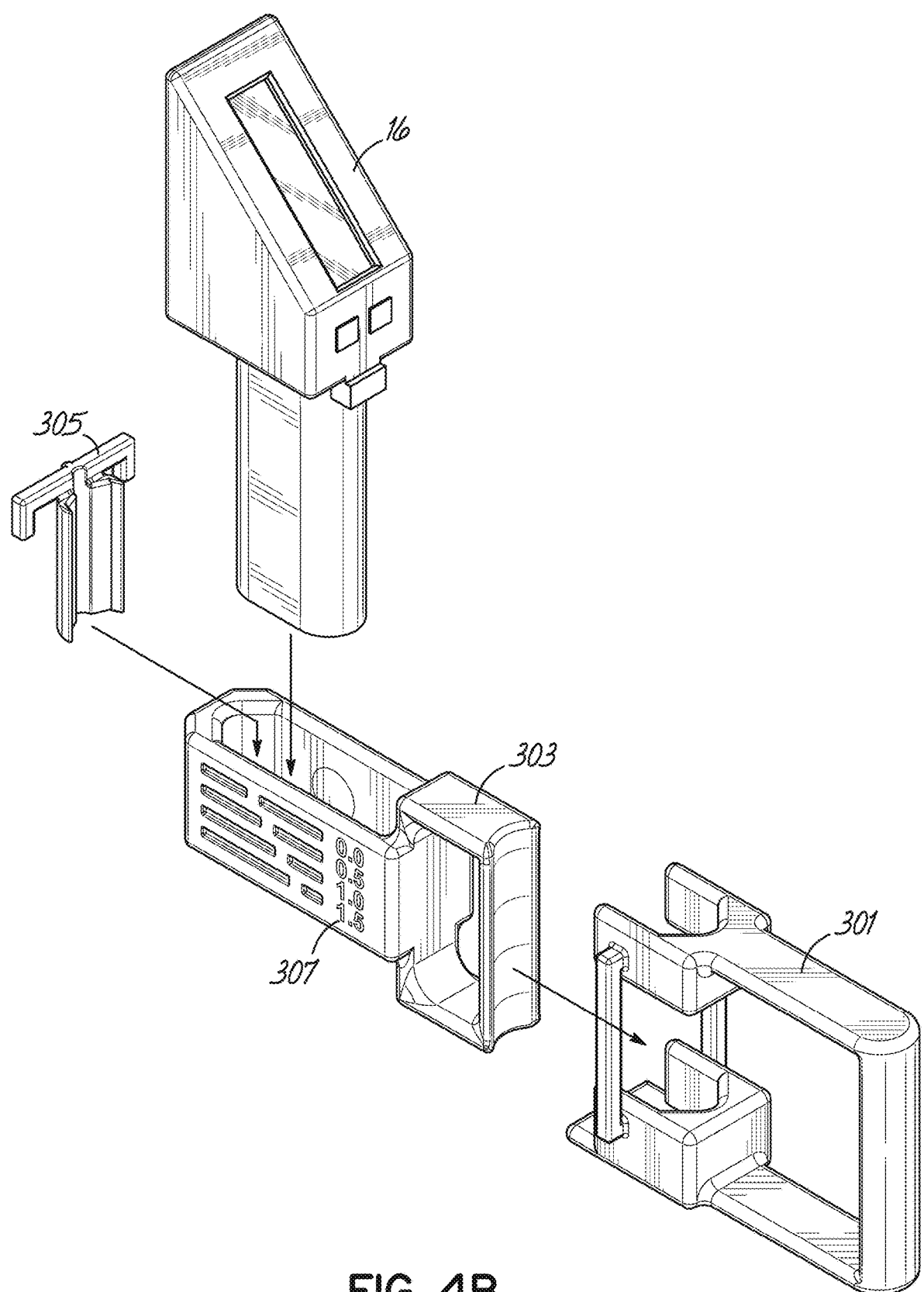
FIG. 4B is a disassembled perspective drawing of the adapter of FIG. 3.
Figure 4C:
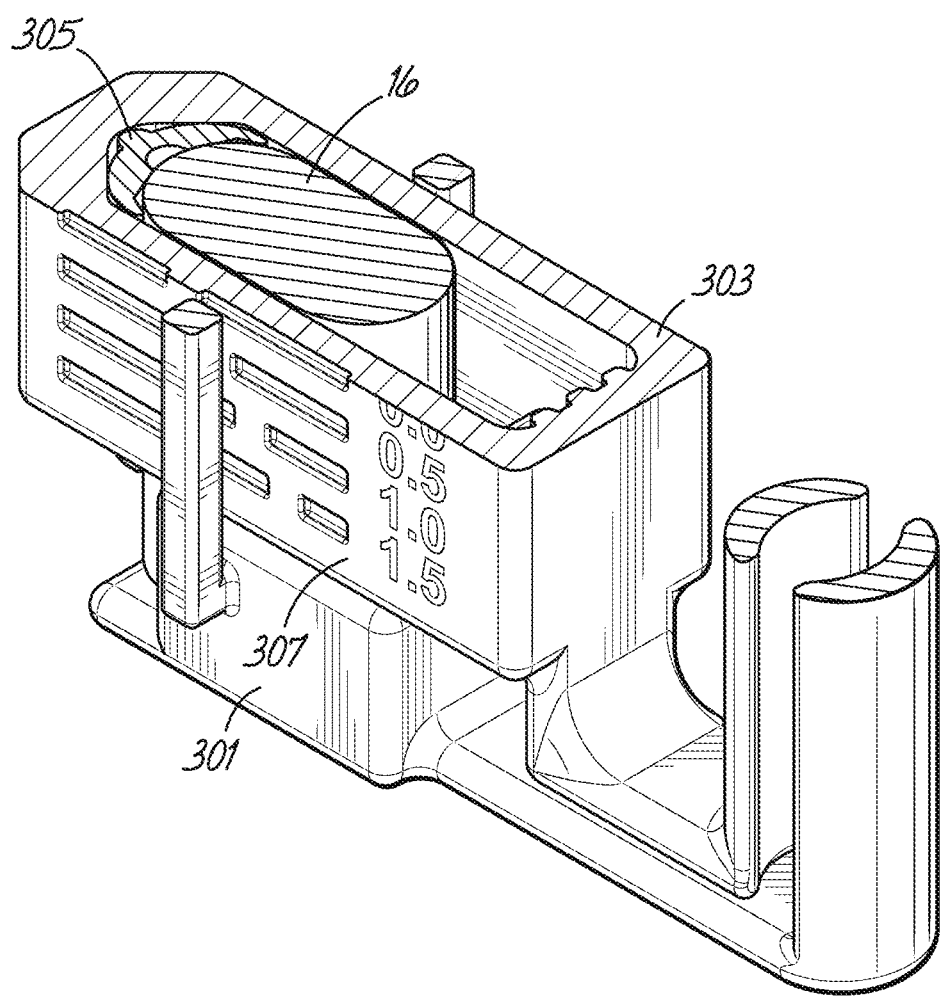
FIG. 4C is a sectional view of the adapter of FIG. 3 taken along line 4C-4C of FIG. 4A.

FIG. 4B is a disassembled perspective drawing of the adapter of FIG. 10 showing the details of the frame 301, slider 303 and insert 305, and FIG. 4C is a cross sectional view showing the spatial relationships of the frame 301, slider 303 and insert 305 when assembled over the hand exercise device 16.

Figure 4D:
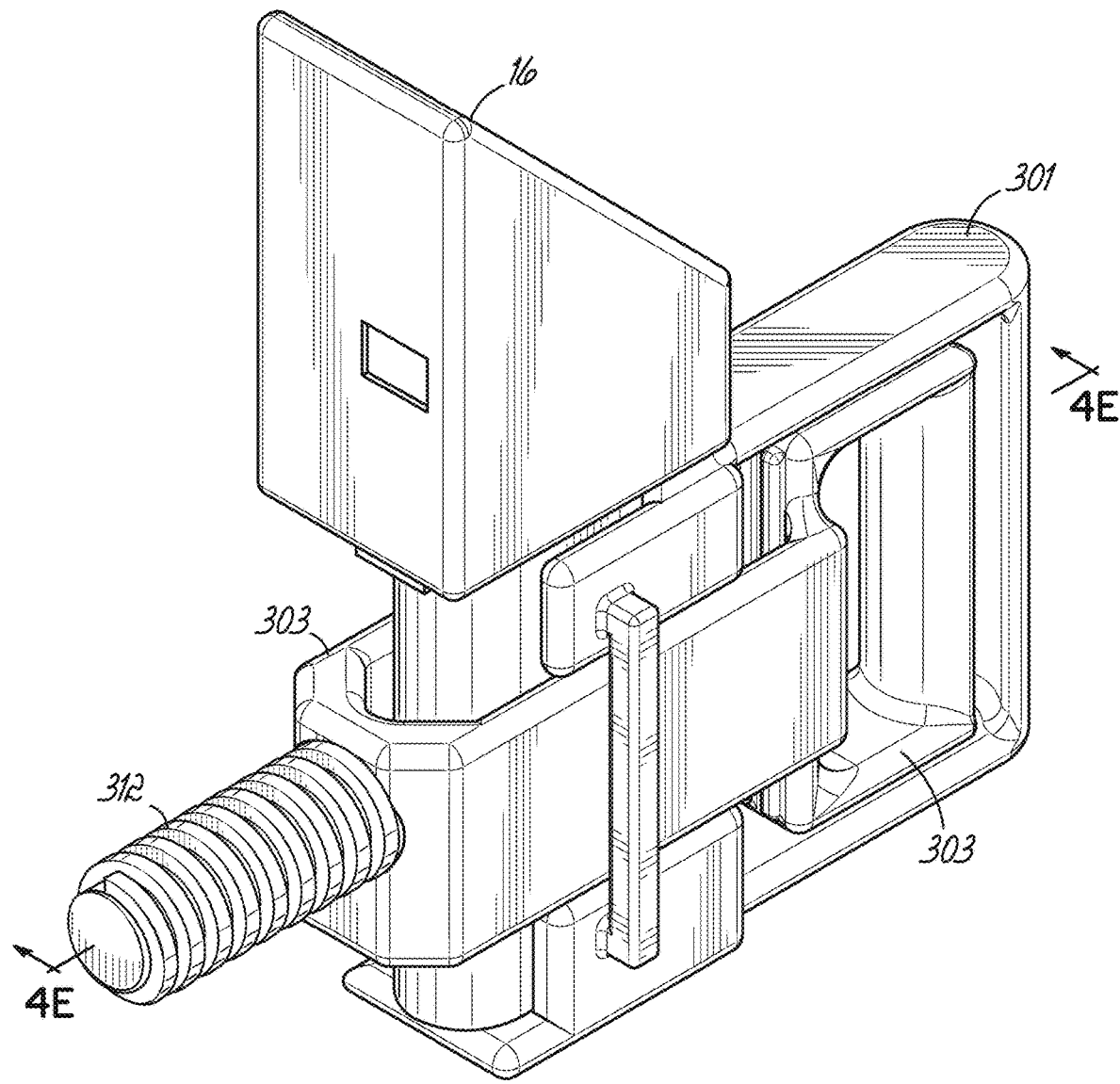
FIG. 4D is a perspective view of an alternative embodiment of an adapter including a screw adjustment for hand size.
Figure 4E:
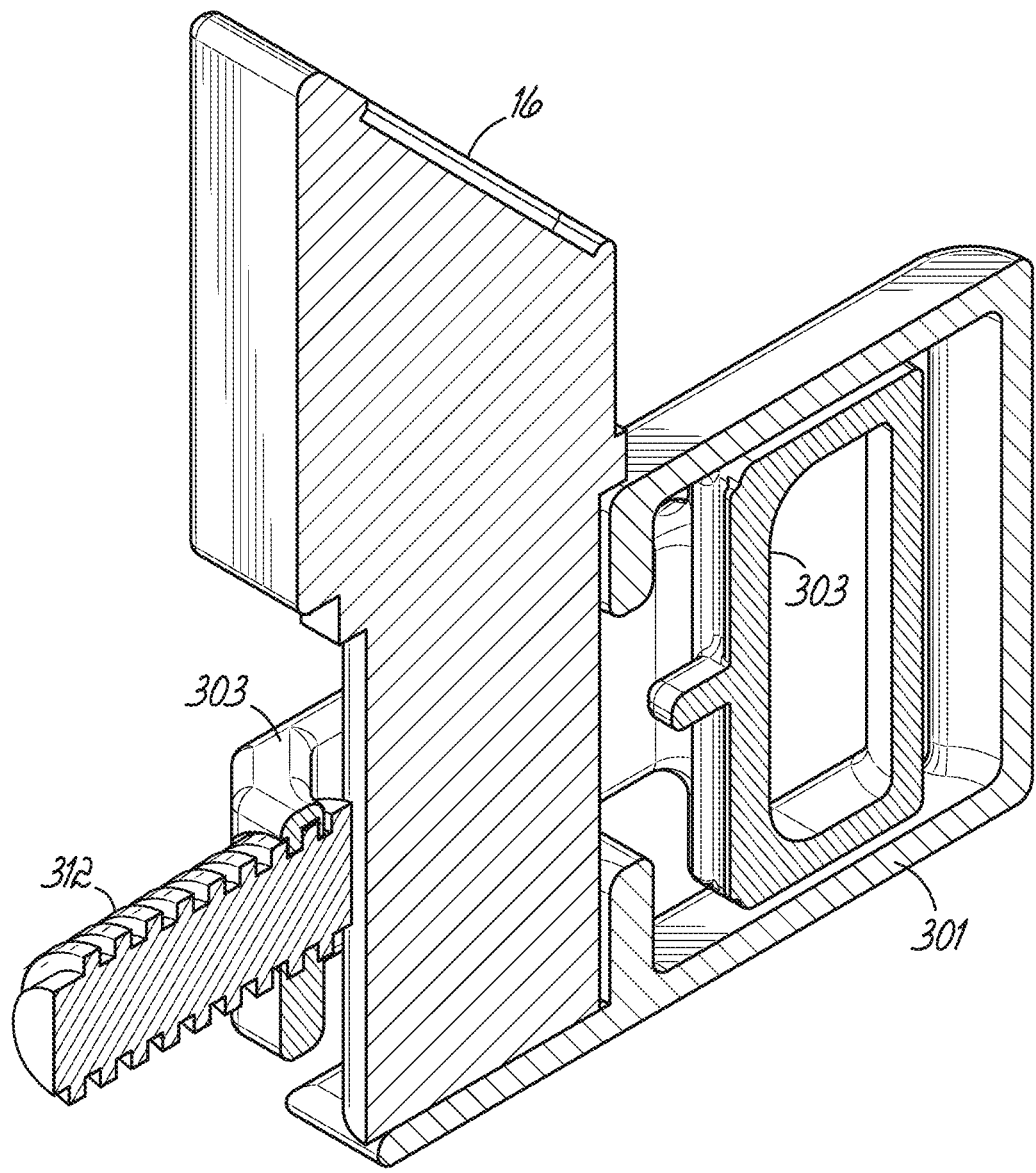
FIG. 4E is a cross sectional view of the adapter of FIG. 3 taken along line 4E-4E of FIG. 4D.
Figure 5A:
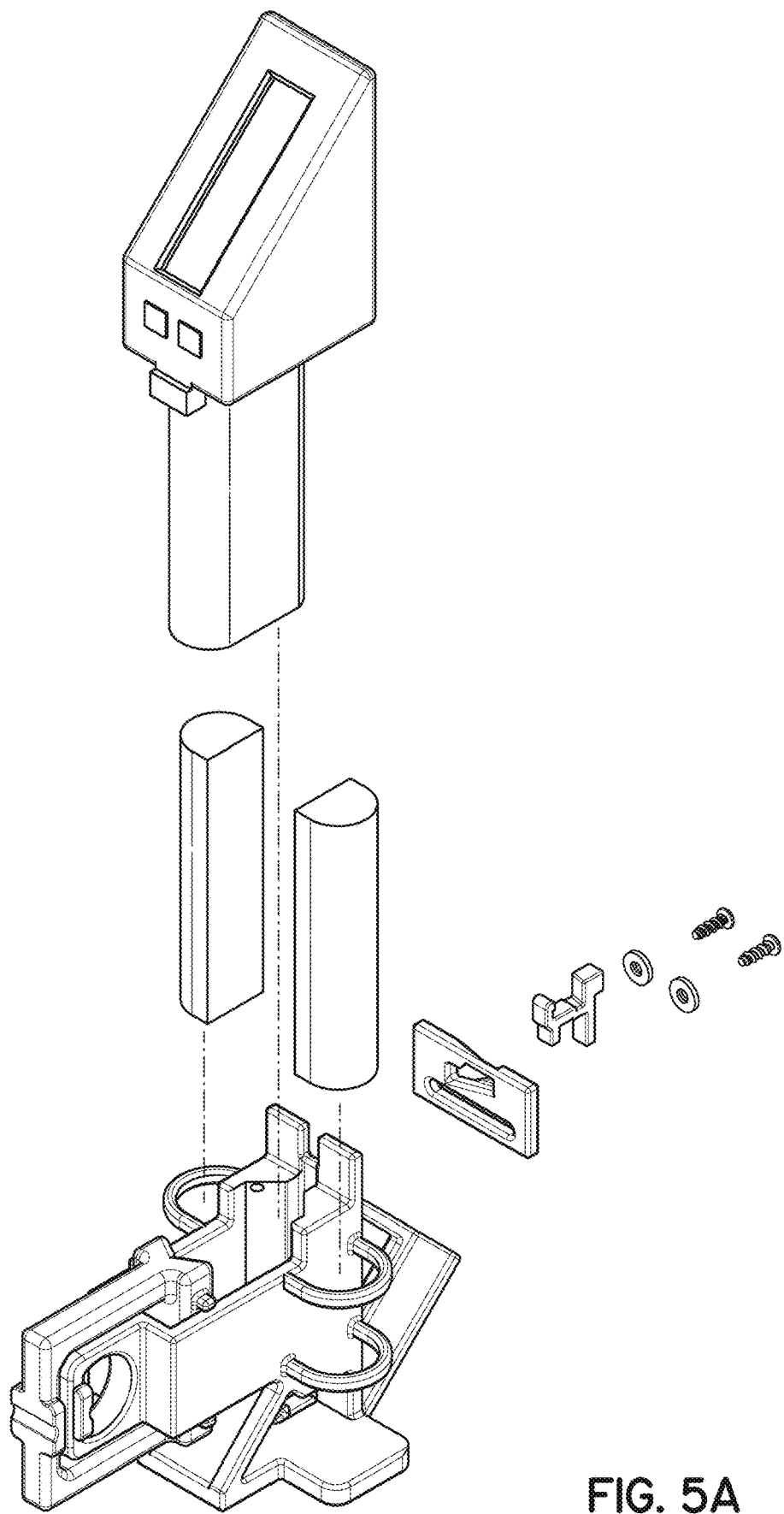
FIG. 5A is an isometric exploded perspective view of an adapter usable with the hand exercise device of FIG. 1, showing the manner in which the device of FIG. 1 is inserted, to adapt the device for an isometric finger exercise (finger pinch) using the device of FIG. 1.
Figure 5B:
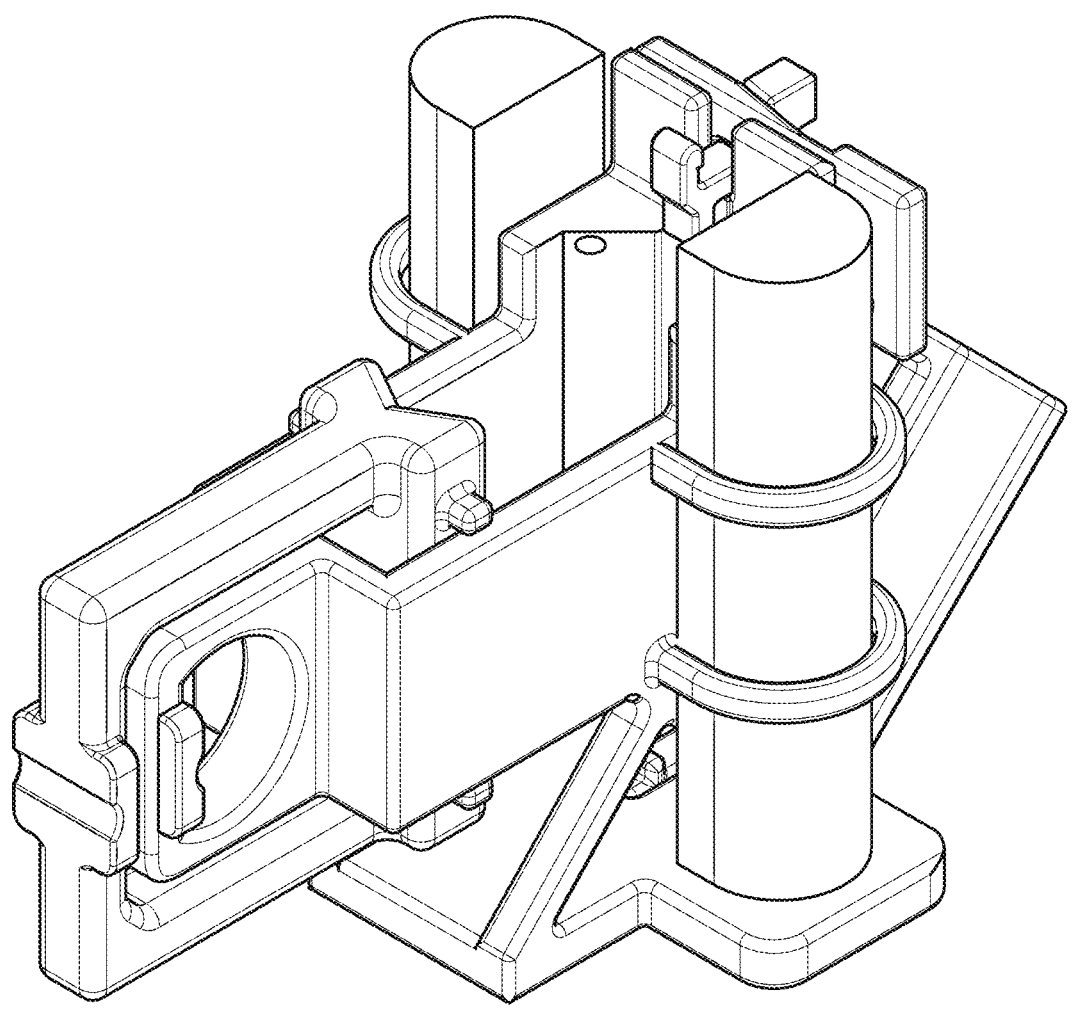
FIG. 5B is an isometric assembled perspective view of the adapter of FIG. 5A.
Figure 5C:
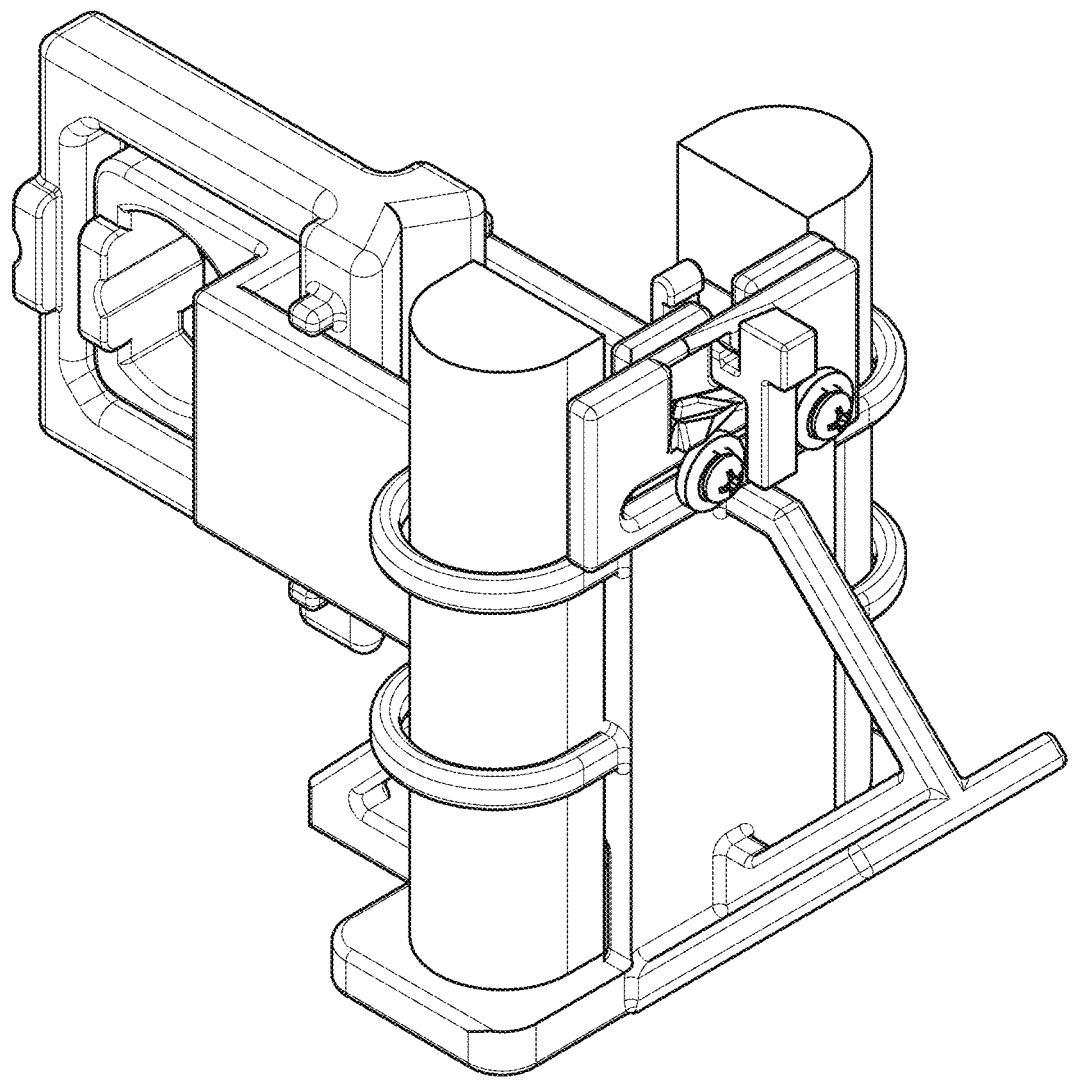
FIG. 5C is a reverse isometric angle assembled perspective view of the adapter of FIG. 5A.
Figure 5D:
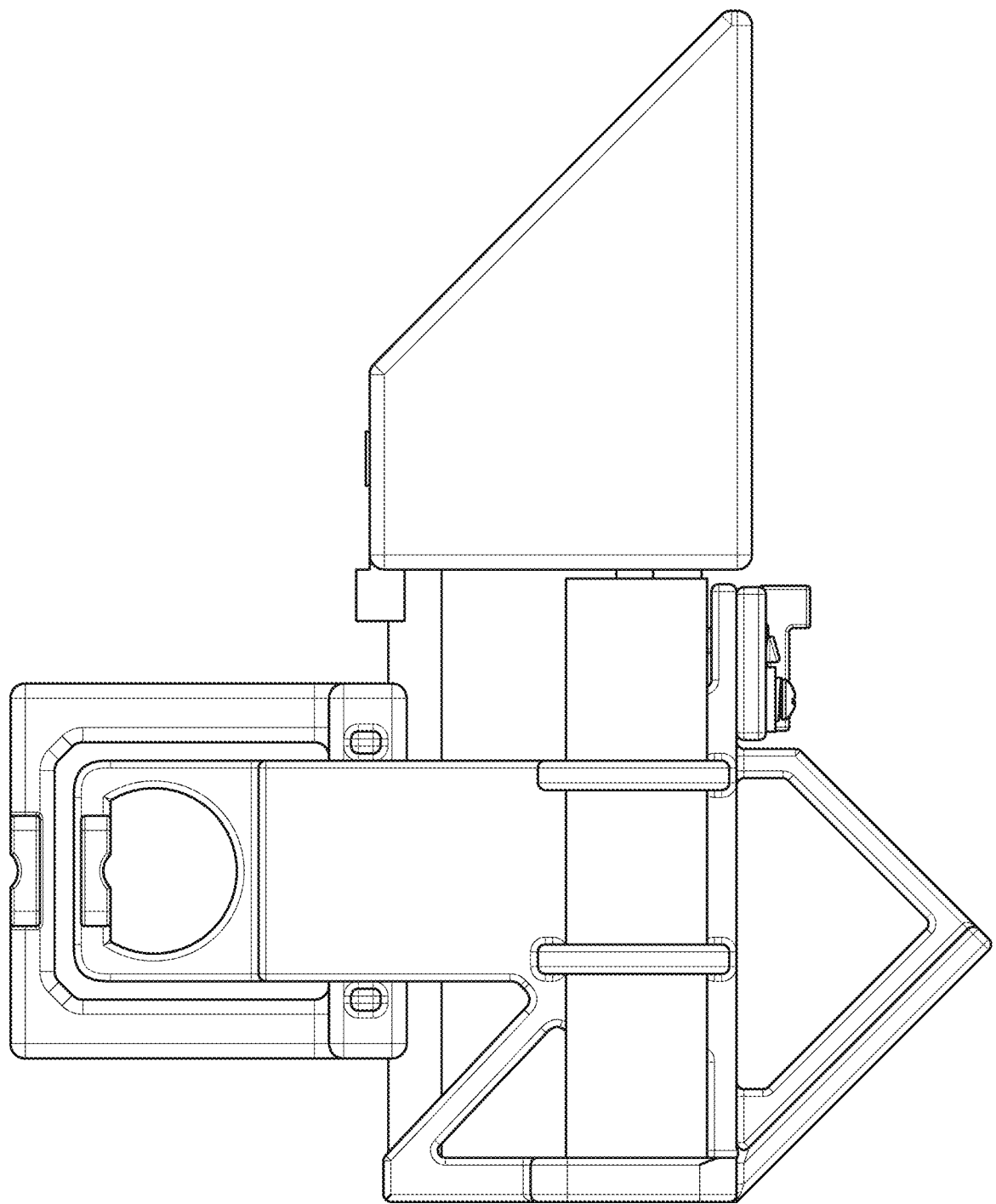
FIG. 5D is a side view of the adapter of FIG. 5A assembled to the device of FIG. 1.
Figure 5E:
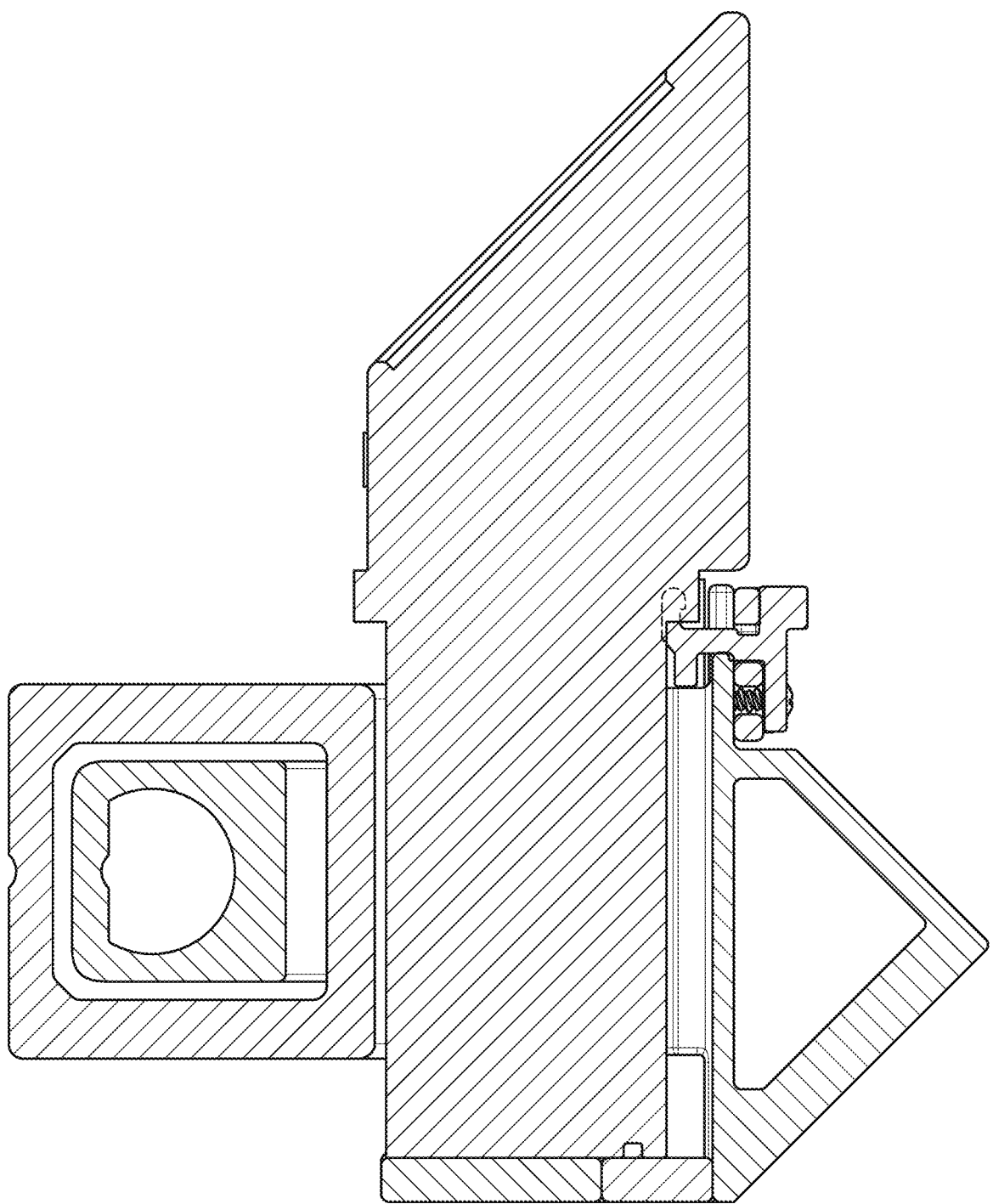
FIG. 5E is a cross sectional view of the adapter of FIG. 5A and device of FIG. 1. showing the manner of engagement of the adapter of FIG. 5A to the sides of the device of FIG. 1.
Figure 6A:
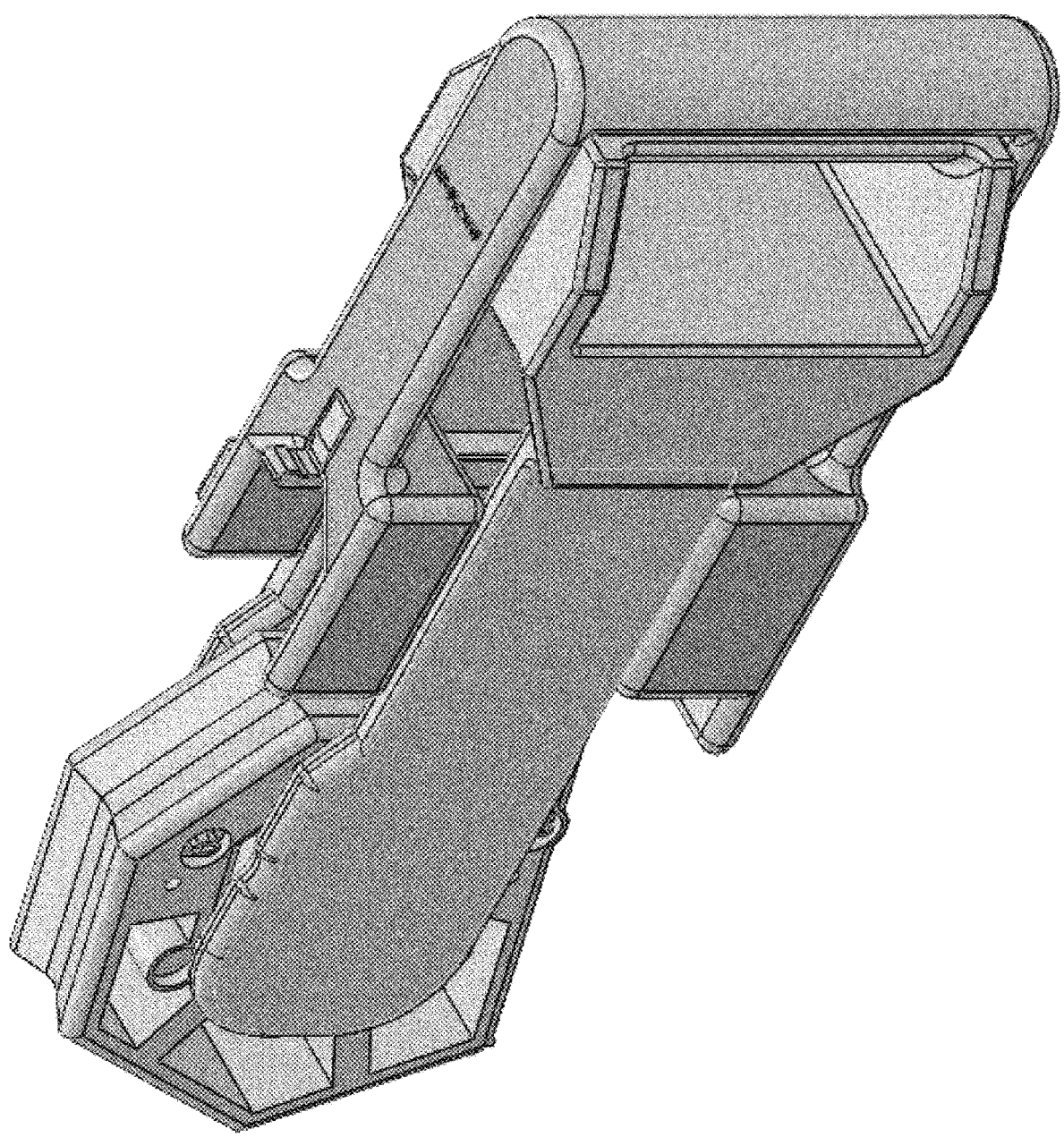
FIG. 6A is an isometric perspective view of an adapter usable with the hand exercise device of FIG. 1 permitting adaptation of the device of FIG. 1 for different hand sizes via the use of a rotary adjustment member.
Figure 6B:
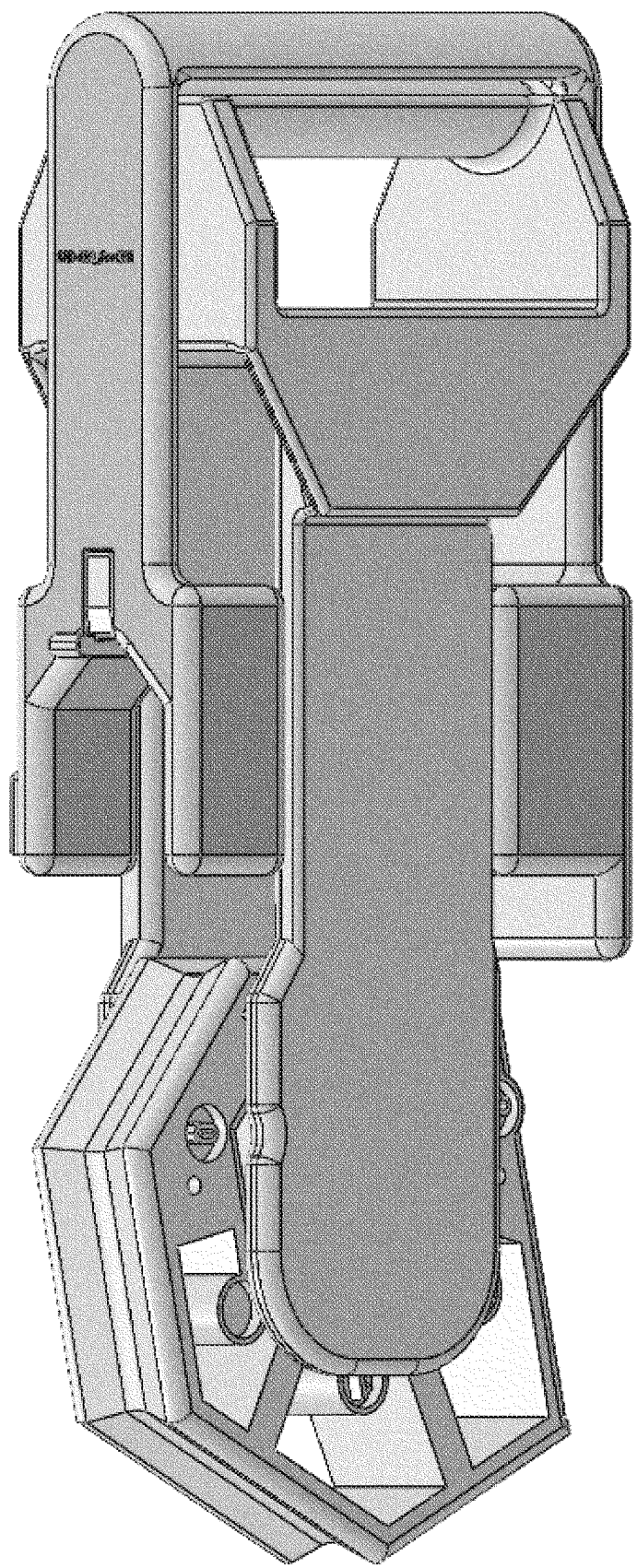
FIG. 6B is a side perspective view of the adapter of FIG. 6A.
Figure 6C:
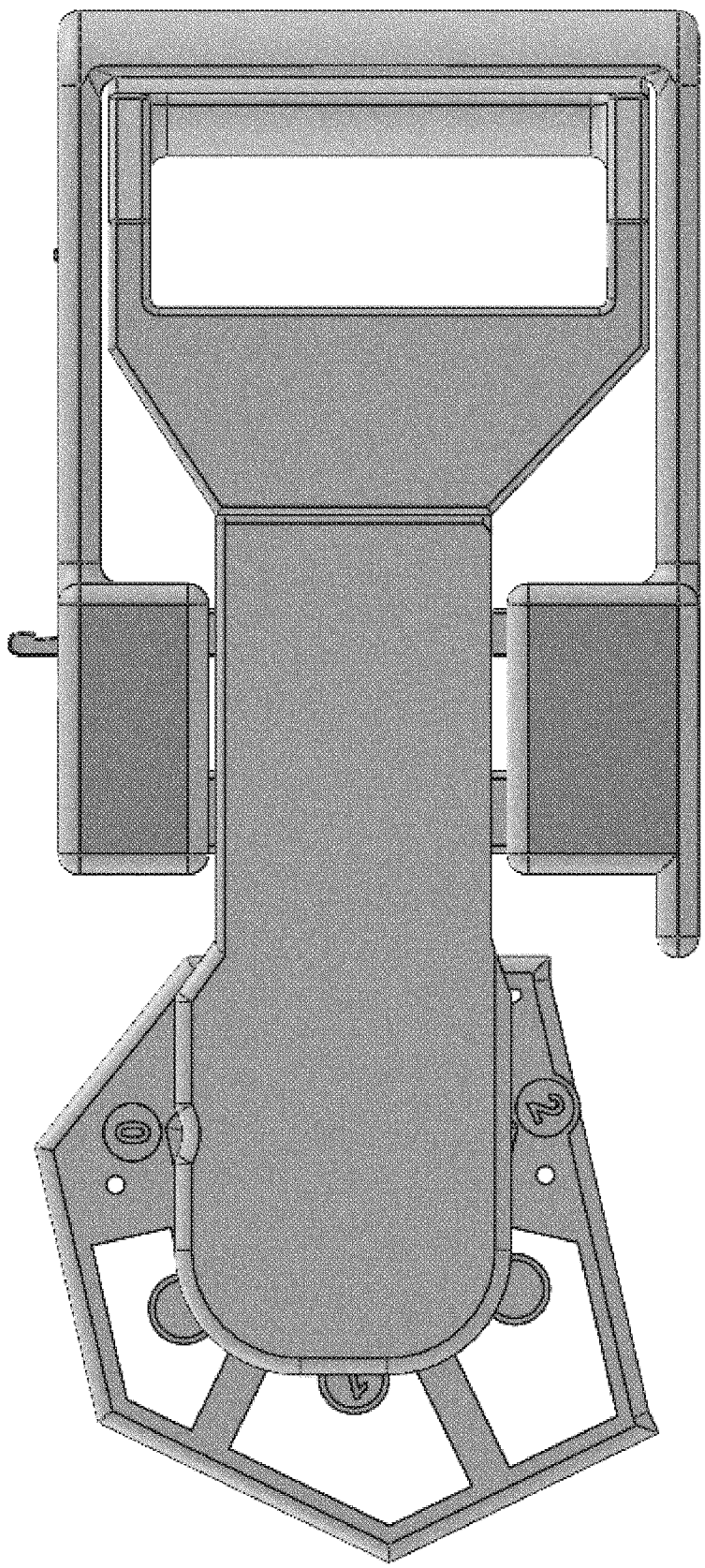
FIG. 6C is a side view of the adapter of FIG. 6A.
Figure 6D:
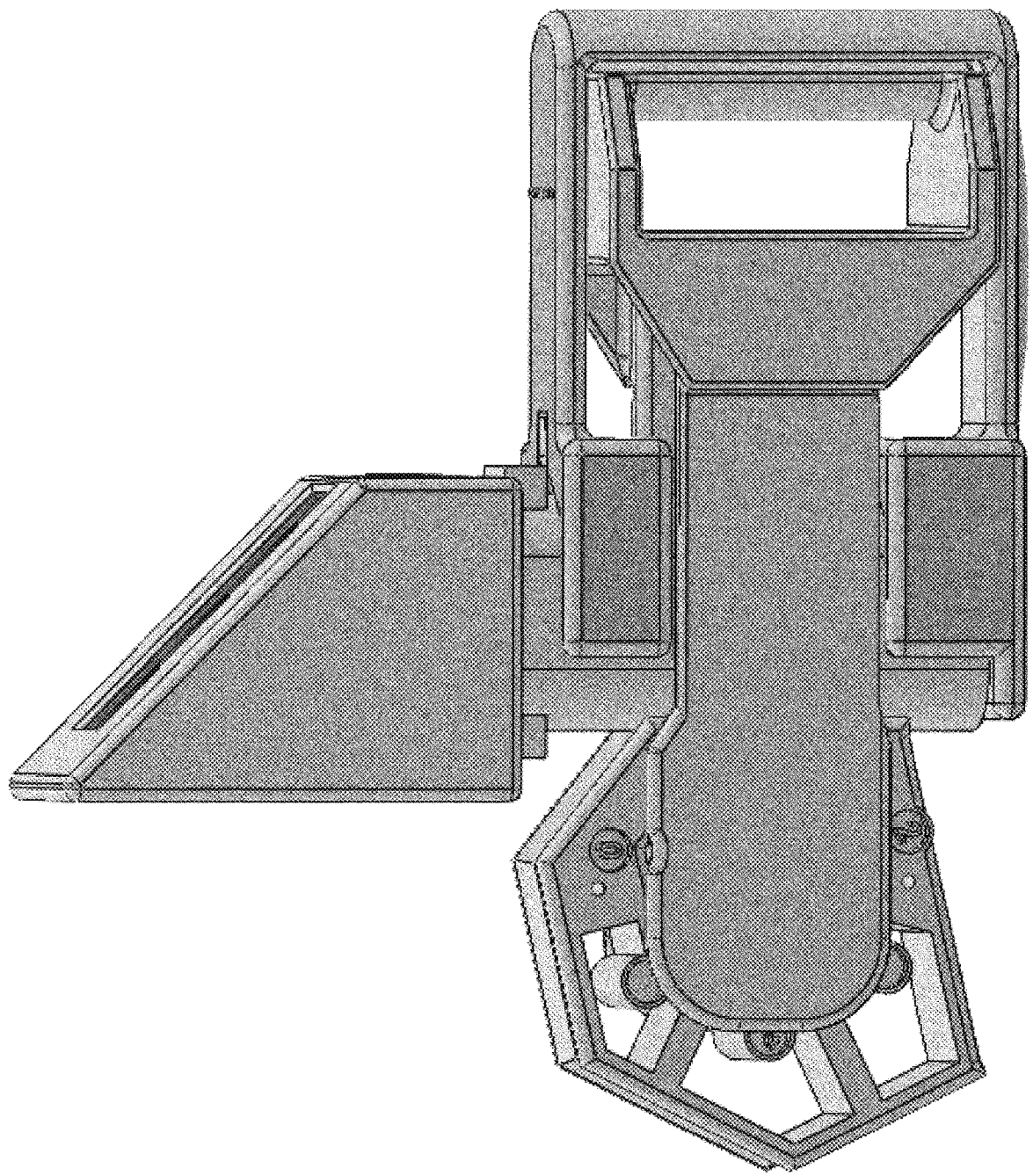
FIG. 6D is a side perspective view of the adapter of FIG. 6A with the device of FIG. 1 installed therein, showing the rotary member rotated to provide the smallest size adjustable gap between the slider and frame of the adapter of FIG. 6A.
Figure 7A:
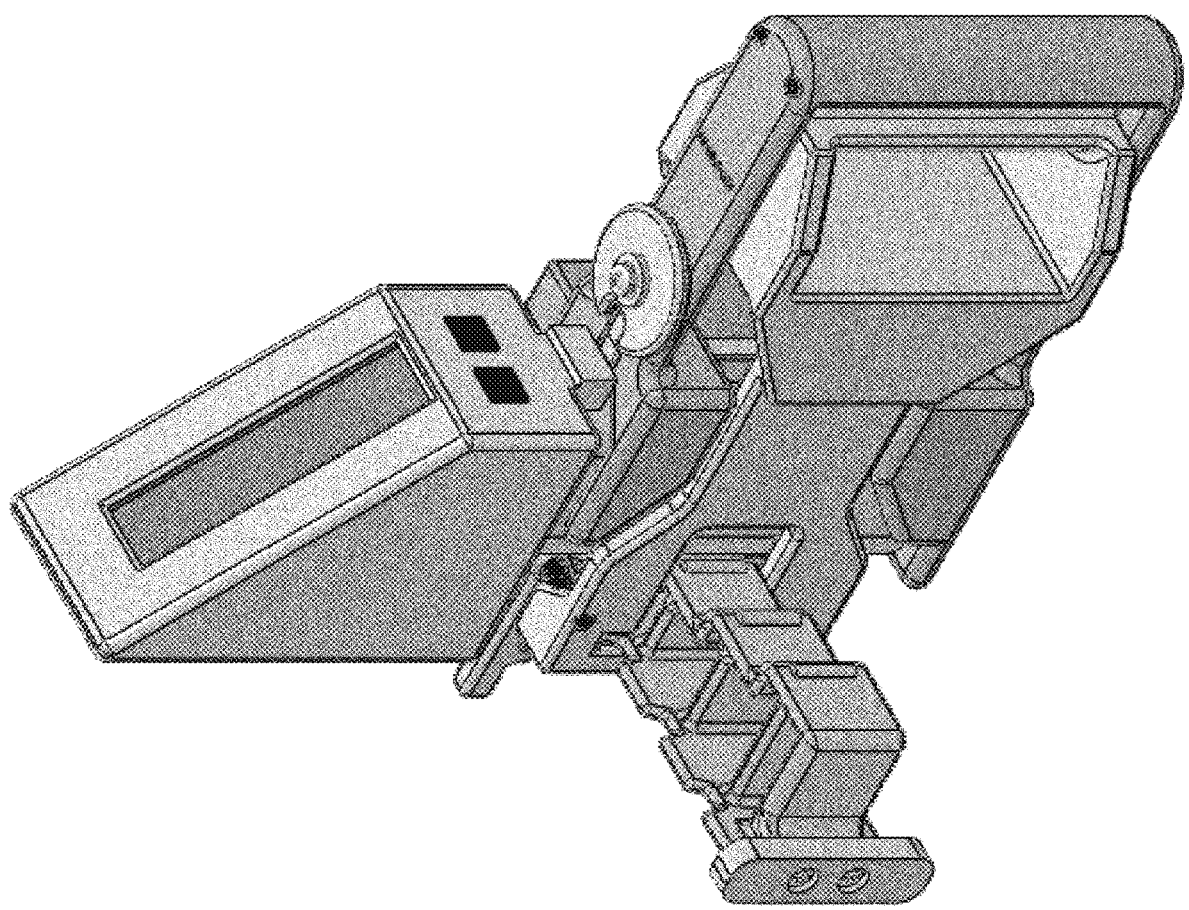
FIG. 7A is an isometric perspective view of an adapter usable with the hand exercise device of FIG. 1, and the device of FIG. 1 installed therein, permitting adaptation of the device of FIG. 1 for different hand sizes via the use of a sliding cam.
Figure 7B:
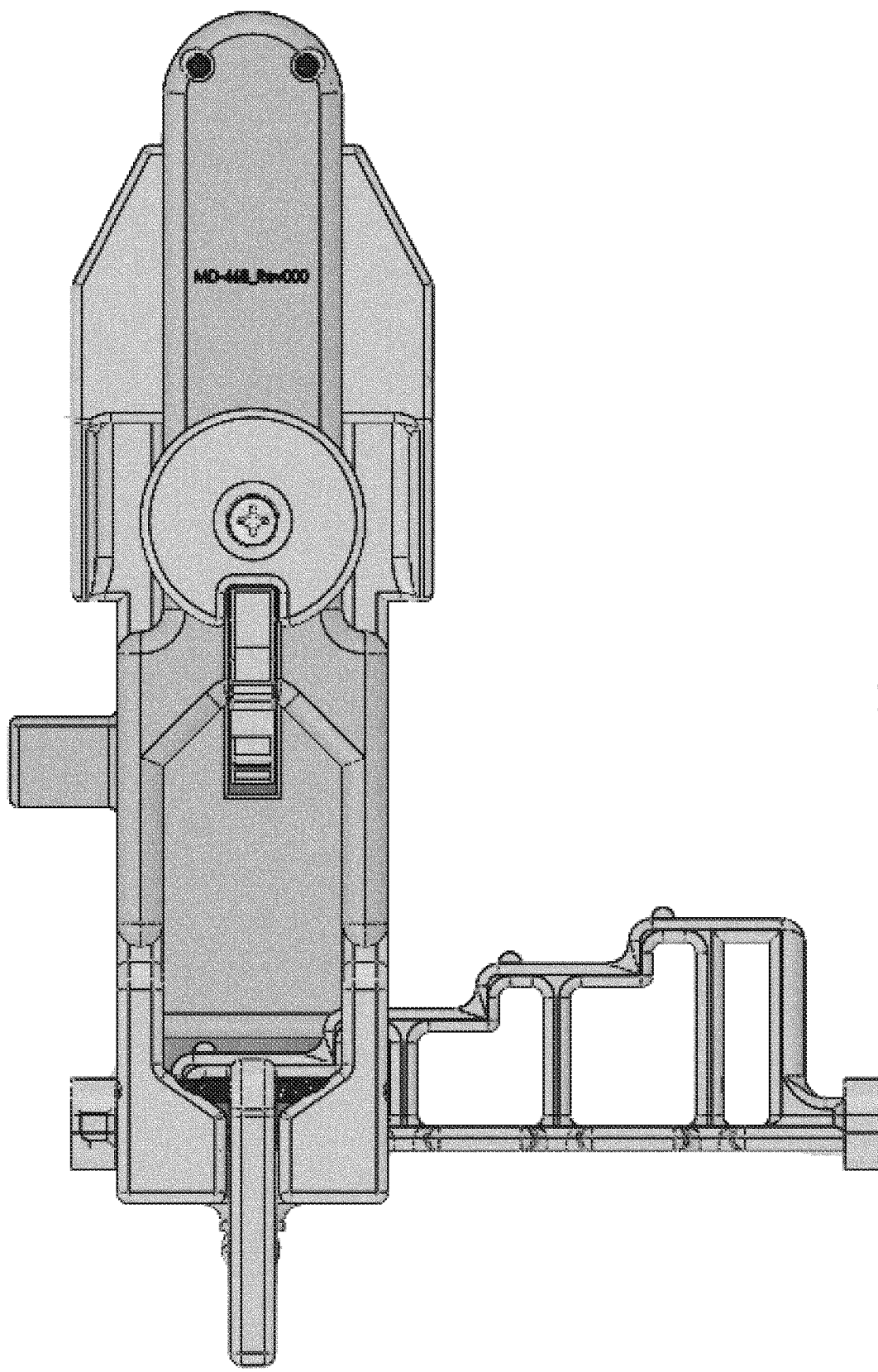
FIG. 7B is top view of the adapter of FIG. 7A.
Figure 7C:
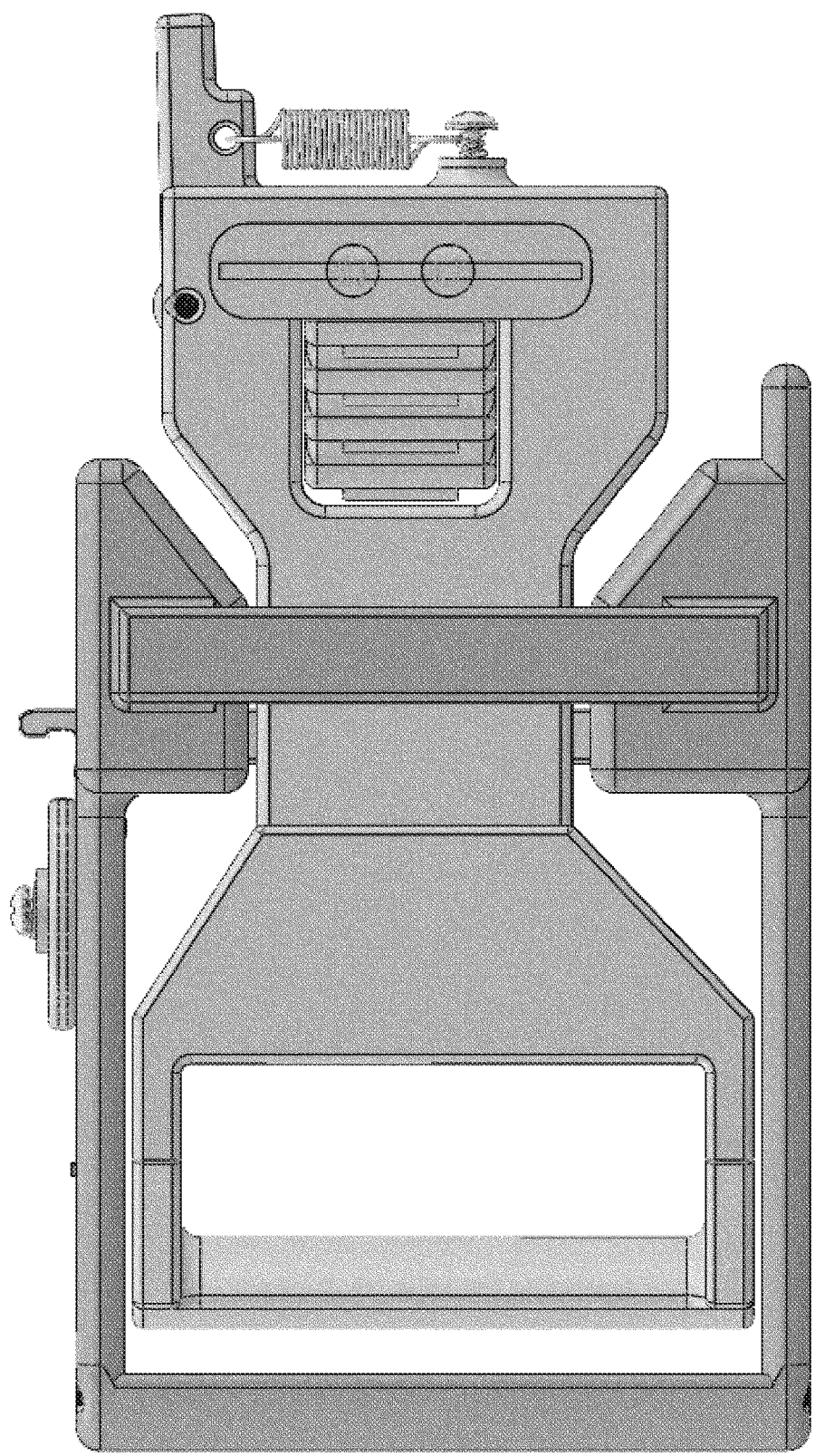
FIG. 7C is a side view of the adapter of FIG. 7A.
Figure 7D:
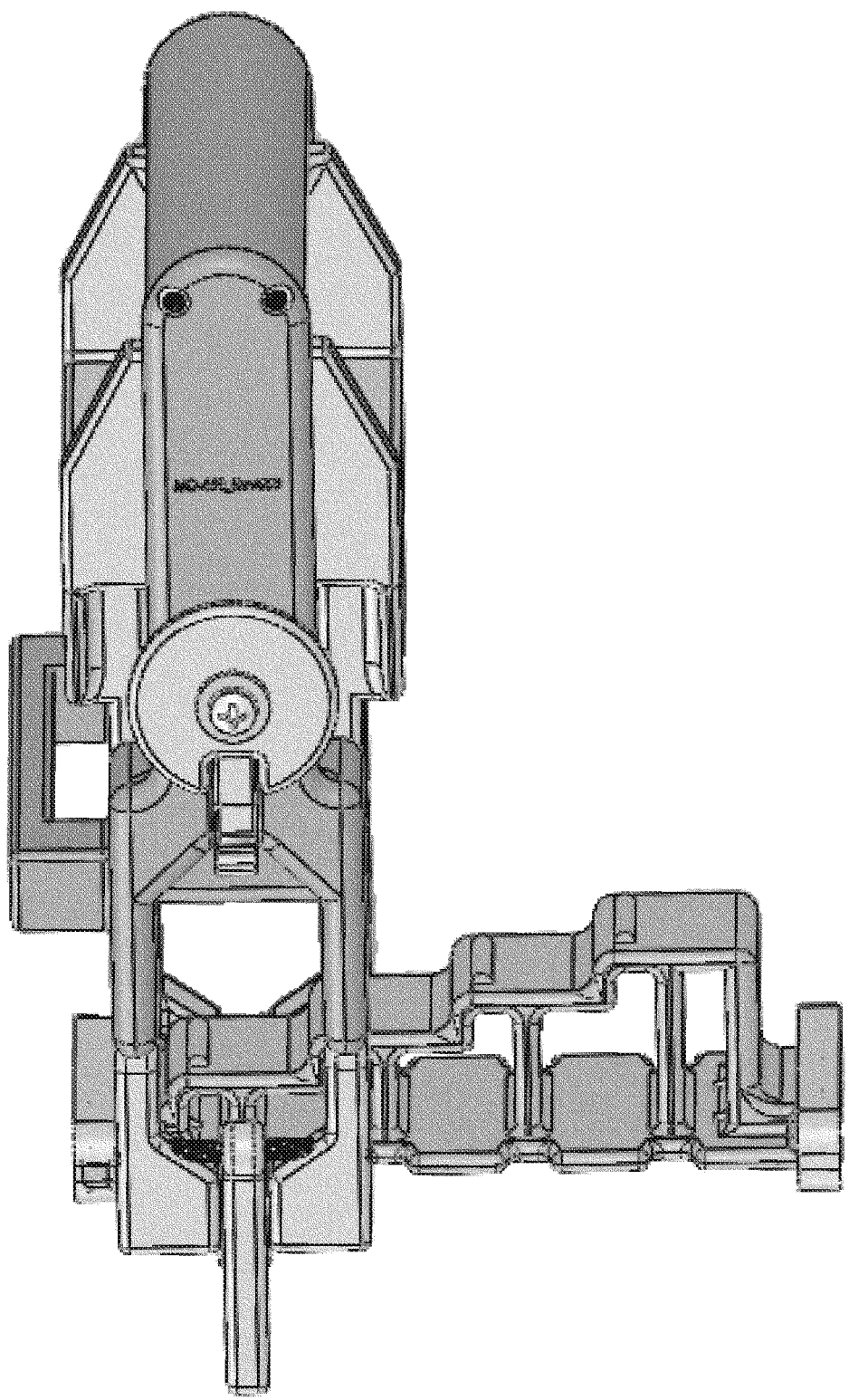
FIG. 7D is a perspective front view of the adapter of FIG. 7A.
Figure 7E:
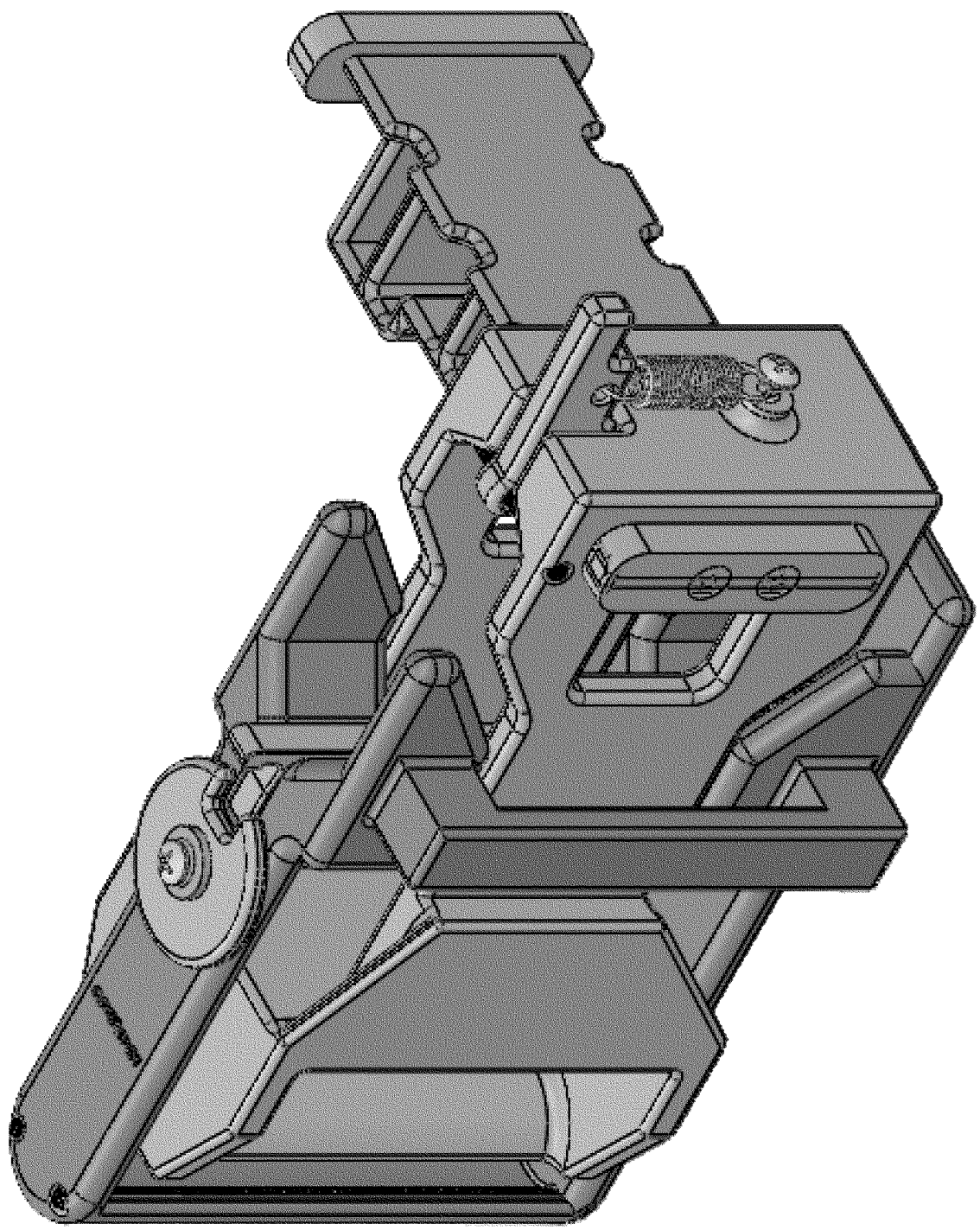
FIG. 7E is a rotated perspective view of the adapter of FIG. 7A.
Figure 7F:
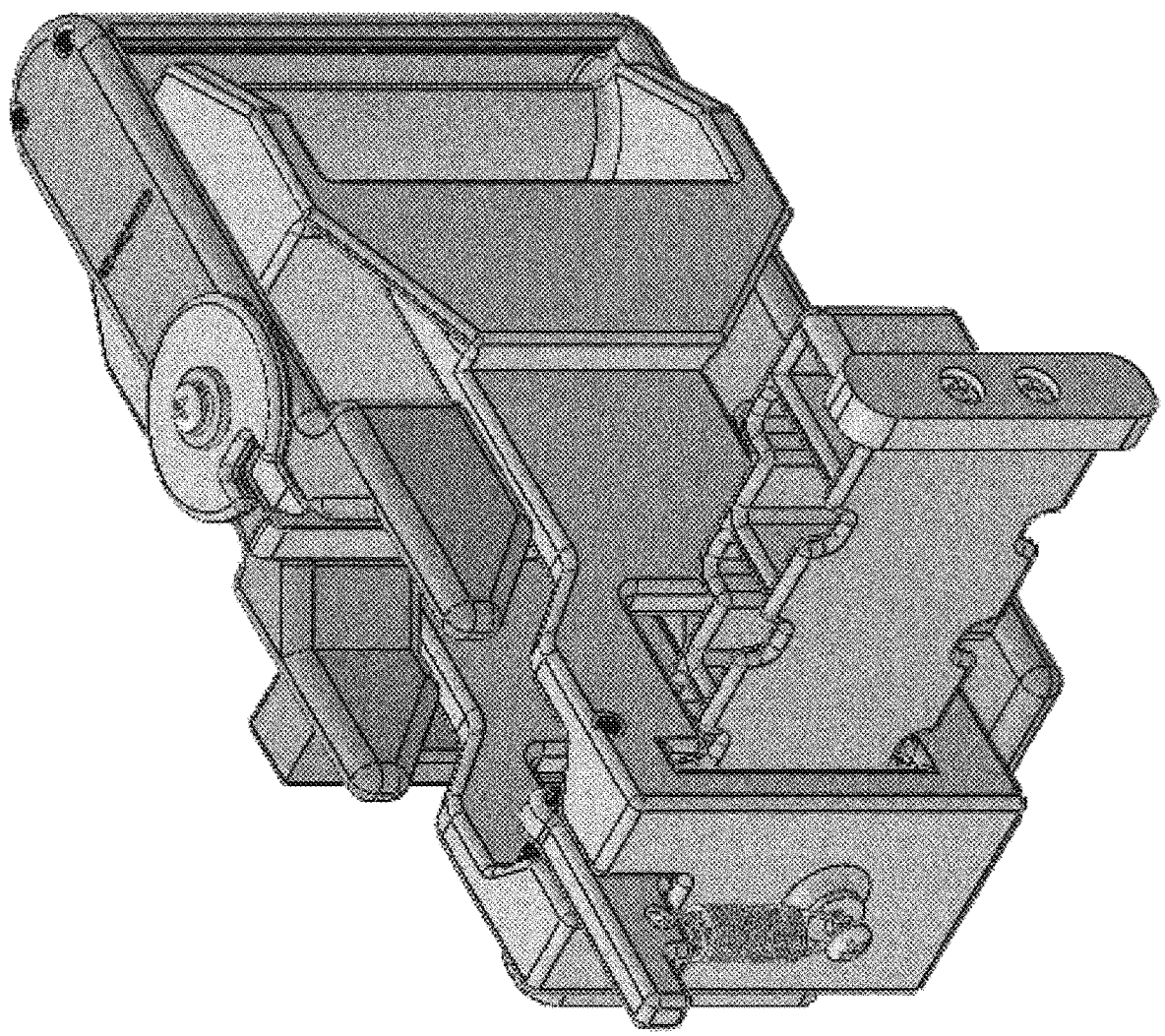
FIG. 7F is a further rotated perspective view of the adapter of FIG. 7A.
Figure 7G:
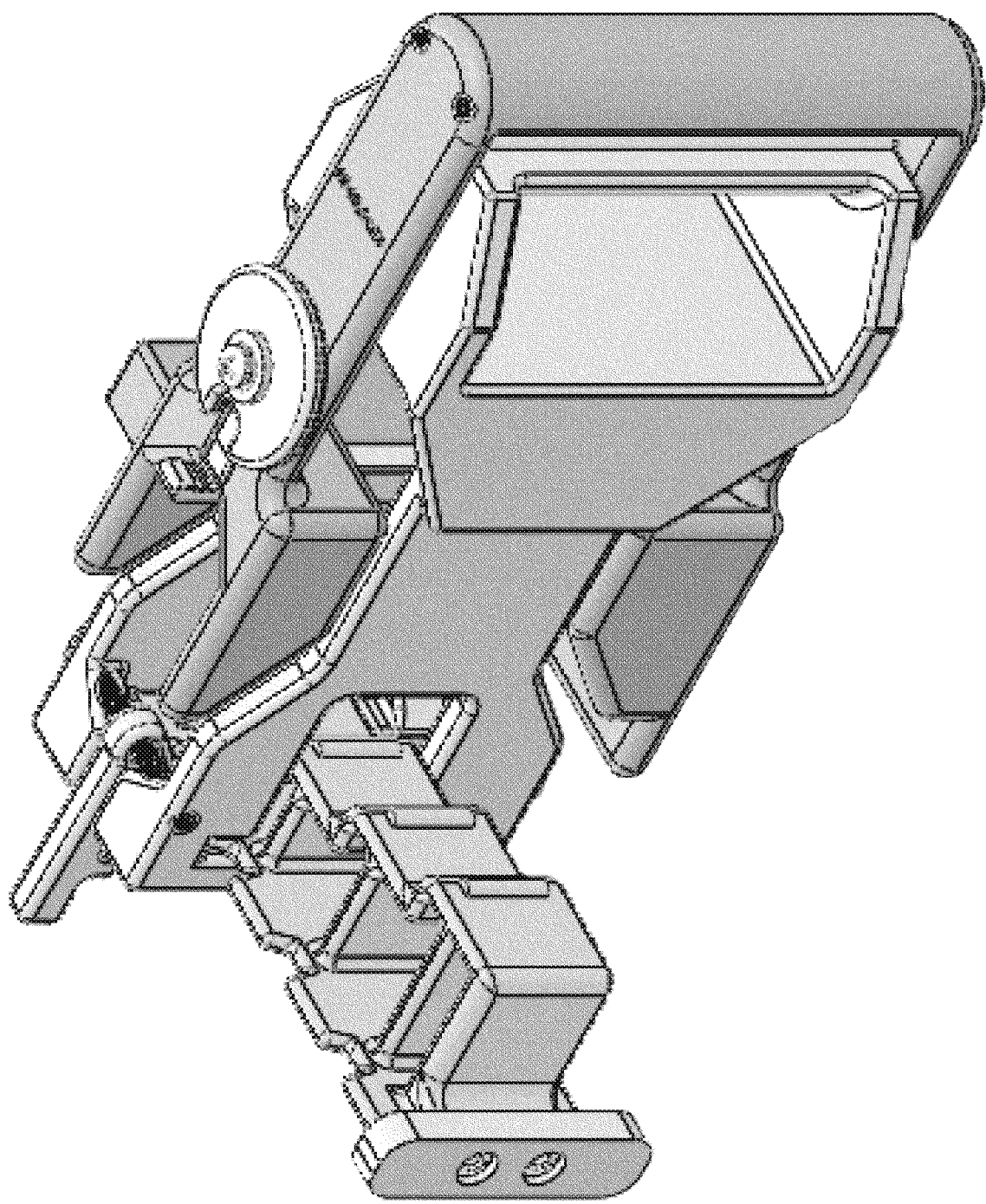
FIG. 7G is an isometric perspective view of the adapter of FIG. 7A with the device of FIG. 1 removed.

An alternate embodiment shown in FIG. 4D does not require the use of an insert, but instead utilizes an integrated adjustment device such as a screw cam 312 that fills the gap between the slider 303 and distal surface (surface facing away from the user) of the built-in grip of the handgrip device 16. As seen in the section view of FIG. 4E adjustment of the screw cam 312 increases or decreases the gap between the slider 303 and distal surface of the built-in grip of device 16, to allow adaptation of the substitute grip for a range of smaller hand sizes.

FIGS. 5A through 5E show an alternative embodiment of an adapter for the device of FIG. 1 which is specifically designed to adapt the device for an isometric finger exercise and finger strength test (finger pinch). As with the other adapters previously described, this adapter includes a frame and a slider, with the device of FIG. 1 fittable between the frame and slider so that finger pressure applied between the frame and slider is transferred to the hand grip of the device of FIG. 1.

FIGS. 6A through 6E illustrate another alternative embodiment of an adapter for the device of FIG. 1. As with the other adapters previously described, this adapter includes a frame and a slider, with the slider holding a rotary cam, and the device of FIG. 1 fittable between the frame and cam wheel and slider, so that grip pressure applied between the frame and slider is transferred to the device of FIG. 1 via the rotary cam. Rotation of the cam allows a different grip spacing between the frame and slider.

FIGS. 7A through 7G illustrate yet another alternative embodiment of an adapter for the device of FIG. 1. In this adapter as with the others, there is a frame and a slider, and the device of FIG. 1 is fittable into the adapter, but in this case a small sliding cam is positioned between the slider and the device of FIG. 1, so that grip pressure applied between the frame and slider is transferred to the device of FIG. 1 via the sliding cam. Movement of the sliding cam allows a different grip spacing between the frame and slider.

In any of the above embodiments, the computer program used in the device of FIG. 1 may be updated to specify operations for new or modified exertion to be performed by a user, e.g., for the adapter of FIG. 2, a specified force and velocity profile governing the exertion, and a specified sequence of repetitions of the exertion. For the adapters of FIGS. 3, 5A, 6A and 7A, the computer program may be adapted for different forces and time periods of exercise and rest expected from a small/child user or a very large person using the adapter, and/or the different forces and time periods of exercise and rest expected when a finger (pinch) exercise is being performed. The computer program instructions may further enable storage an identity of the user and corresponding MVC for the user with reference to the adapter used, a matrix of muscle group exertions for each adapter and/or user, repetitions for each adapter and/or user, and rest periods for each adapter and/or user (e.g., based on a percentage of the MVC), a selection of an exercise regimen for each adapter and/or user, data related to an exercise regimen performed by a user for each adapter regarding a degree to which the user complies with the exercise protocol, and a date and time of an exercise regimen performed by a user and the adapter used along with parameters related to the exercise regimen.

Parameters related to a range of motion (e.g., adapter setup position or, in the case of the adapter of FIG. 2, start position and end position) may also be determined and stored with respect to the adapter. The computer program instructions may further specify protocols for receiving user input. For example, when executed by a processor, the computer program instructions may control the processor to display a menu of user-selectable options on a display device. The computer program instructions may further cause the processor to receive user selections from a graphical user input device. For example, a person having small physical features may select a smaller range of motion in the exercise relative to a user having larger physical features. As a further example, the processor may receive information regarding a muscle group to be exercised, a machine ID, etc., which establishes parameters for the particular machine. Parameters may include force levels, ranges of motion, MVC measurement position, etc.

The Summary and Abstract sections may set forth one or more but not all example embodiments and thus are not intended to limit the scope of embodiments of the invention and the appended claims in any way.

Embodiments have been described above with the aid of functional building blocks illustrating the implementation of specified functions and relationships thereof. The boundaries of these functional building blocks have been arbitrarily defined herein for the convenience of the description. Alternate boundaries can be defined to the extent that the specified functions and relationships thereof are appropriately performed.

The foregoing description of specific embodiments will so fully reveal the general nature of embodiments of the invention that others can, by applying knowledge of those of ordinary skill in the art, readily modify and/or adapt for various applications such specific embodiments, without undue experimentation, without departing from the general concept of embodiments of the invention. For example, principles of the present invention may be applied to adapting a hand dynamometer device into other applications to measure applied force; for example adapters such as those described herein could be used to adapt a hand dynamometer device to measure the weight of items positioned such that their weight is applied between the frame and slider of the adapter. With such an application weights between 1 and 200 pounds could be readily weighed, e.g., as part of package shipping. Therefore, such adaptation and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the specification is to be interpreted by persons of ordinary skill in the relevant art in light of the teachings and guidance presented herein.

The breadth and scope of embodiments of the invention should not be limited by any of the above-described example embodiments, but should be defined only in accordance with the following claims and their equivalents.

What is claimed is:

1. An adapter for a hand exercise and hand strength device having a force sensor for detecting the force applied by a hand between a first and second handgrip surface of the device, the adapter comprising:
   a frame engaging the first surface of the device and having a first replacement grip surface thereon, and
   a slider engaging the frame and the second surface of the device and having a second replacement grip surface thereon,
   the slider and frame coupling mechanical exertion applied to the first and second replacement grip surfaces to the first and second handgrip surfaces of the hand exercise device.

2. The adapter of claim 1 further comprising:
   a piston and cylinder;
      the piston and cylinder positioned between the slider and the second handgrip surface of the hand exercise device,
      the piston and cylinder being movable relative to each other in a range of motion, such that the first and second replacement grip surfaces move relative to each other in a range of motion during a hand exercise.

3. The adapter of claim 2 further comprising
   a displacement sensor measuring the distance of motion of the piston and cylinder relative to each other,
   an actuator for applying force between the piston and cylinder.

4. The adapter of claim 3 wherein the displacement sensor and actuator are coupled to a control circuit within the hand exercise device for control of the actuator according to a specified force and/or velocity profile to provide a hand exercise to the user according to one or more of:
   an isometric exercise comprising a specified force profile with zero fixed velocity;
   an isokinetic exercise comprising a fixed non-zero velocity and constant or variable force;
   an isotonic exercise comprising a constant force with constant or variable non-zero velocity; and
   an isodynamic exercise comprising an isokinetic or isotonic exercise combined with an isometric exercise.

5. The adapter of claim 3 further comprising
   a control circuit;
      the control circuit coupled to the actuator, displacement sensor and a force sensor within the hand exercise device for control of the actuator according to a specified force and/or velocity profile to provide a hand exercise to the user according to one or more of:
      an isometric exercise comprising a specified force profile with zero fixed velocity;
      an isokinetic exercise comprising a fixed non-zero velocity and constant or variable force;
      an isotonic exercise comprising a constant force with constant or variable non-zero velocity; and
      an isodynamic exercise comprising an isokinetic or isotonic exercise combined with an isometric exercise.

6. The adapter of claim 1 further comprising:
   a cam;
      the cam being positionable between the slider and the second handgrip surface of the hand exercise device,
      the cam being movable to at least a first and a second position, the first and second replacement grip surfaces being spaced differently when the cam is in the first position than when the cam is in the second position.

7. The adapter of claim 6 wherein in the first position the cam is between the slider and second handgrip surface, and in the second position the cam is not between the slider and second handgrip surface.

8. The adapter of claim 6 wherein the cam is a screw member positioned between the slider and the second handgrip surface, wherein the screw member is movable by rotation such that a greater or lesser extent of the cam is positioned between the slider and second handgrip surface.

9. The adapter of claim 6 wherein the cam is a rotary member positioned between the slider and the second handgrip surface, wherein the rotary member is movable by rotation such that a greater or lesser radial extent of the cam is positioned between the slider and second handgrip surface.

10. The adapter of claim 6 wherein the cam is a slidable member position between the slider and the second handgrip surface, wherein the slidable member is movable by sliding such that a thicker or thinner portion of the cam is positioned between the slider and second handgrip surface.

11. The adapter of claim 1 wherein the first and second replacement grip surfaces are sized for gripping by fewer than all of the fingers of a user's hand.

12. The adapter of claim 11 wherein the first and second replacement grip surfaces are sized for gripping by a user's finger and thumb, for performing pinch exercises and pinch tests.

* * * * *